US010767214B2

(12) United States Patent
LaPointe et al.

(10) Patent No.: US 10,767,214 B2
(45) Date of Patent: Sep. 8, 2020

(54) METHOD OF MICROVESICLE ENRICHMENT

(75) Inventors: Lawrence Charles LaPointe, North Ryde (AU); Susanne Kartin Pedersen, North Ryde (AU); Aidan McEvoy, North Ryde (AU)

(73) Assignee: CLINICAL GENOMICS PTY LTD, Elsternwick, Victoria (AU)

( * ) Notice: Subject to any disclaimer, the term of this patent is extended or adjusted under 35 U.S.C. 154(b) by 460 days.

(21) Appl. No.: 14/354,111

(22) PCT Filed: Oct. 26, 2011

(86) PCT No.: PCT/AU2011/001371
§ 371 (c)(1),
(2), (4) Date: Aug. 5, 2014

(87) PCT Pub. No.: WO2012/054975
PCT Pub. Date: May 3, 2012

(65) Prior Publication Data
US 2015/0010951 A1 Jan. 8, 2015

(51) Int. Cl.
*C12Q 1/6806* (2018.01)
*G01N 33/00* (2006.01)

(52) U.S. Cl.
CPC .................. *C12Q 1/6806* (2013.01)

(58) Field of Classification Search
CPC .................................................. C12Q 1/6806
See application file for complete search history.

(56) References Cited

U.S. PATENT DOCUMENTS

| | | | |
|---|---|---|---|
| 4,683,195 A | 7/1987 | Mullis et al. | 435/6.11 |
| 4,683,202 A | 7/1987 | Mullis | 435/91.2 |
| 4,965,188 A | 10/1990 | Mullis et al. | 435/6.12 |
| 5,035,996 A | 7/1991 | Hartley | 435/6.11 |
| 5,234,809 A | 8/1993 | Boom et al. | 435/91.2 |
| 5,310,652 A | 5/1994 | Gelfand et al. | 435/6.11 |
| 5,322,770 A | 6/1994 | Gelfand | 435/5 |
| 5,407,800 A | 4/1995 | Gelfand et al. | 435/6.11 |
| 5,638,896 A | 6/1997 | Nishino et al. | 165/132 |
| 5,945,313 A | 8/1999 | Hartley et al. | 435/91.2 |
| 6,287,823 B1 | 9/2001 | Hartley | 435/91.2 |
| 6,518,026 B2 | 2/2003 | Hartley | 435/6.12 |
| 6,905,825 B2 | 6/2005 | Kojima et al. | 210/656 |
| 8,669,050 B2 | 3/2014 | James et al. | 435/6.1 |
| 2002/0192667 A1 | 12/2002 | Kojima et al. | 210/656 |
| 2003/0059444 A1 | 3/2003 | Zollinger et al. | 424/249.1 |
| 2005/0053967 A1 | 3/2005 | James et al. | 435/6.11 |
| 2009/0325810 A1 | 12/2009 | Lapointe et al. | 506/7 |
| 2010/0292094 A1 | 11/2010 | Lapointe et al. | 506/9 |
| 2011/0098189 A1 | 4/2011 | Lapointe et al. | 506/9 |
| 2011/0160072 A1 | 6/2011 | Lapointe et al. | 506/9 |
| 2012/0115160 A1* | 5/2012 | D'Souza-Schorey | G01N 33/5076 435/7.1 |
| 2013/0338020 A1 | 12/2013 | Ross et al. | 506/9 |
| 2014/0155280 A1 | 6/2014 | Lapointe et al. | 506/7 |

FOREIGN PATENT DOCUMENTS

| | | |
|---|---|---|
| EP | 0 389 063 | 8/1997 |
| WO | WO 2007/064859 | 6/2007 |
| WO | WO 2009/100029 | * 8/2009 |

OTHER PUBLICATIONS

Nucleic Acid Isolation and Purification Product Selection Guide, Roche, pp. 1-24 (2010).*
Pfister, R.R. et al., Invest. Ophtalmol. Visual Sci., vol. 37, pp. 230-237 (1996).*
mirVana miRNA isolation kit booklet, pp. 1-33 (Jan. 2011).*
Pegtel, D.M. et al., PNAS USA, vol. 107, pp. 6328-6333 and supporting pp. 1-9 (2010).*
Dynal "Gene Expression in Focus", pp. 1-8 (2001).*
TaqMane® EZ RT-PCR Kit from Applied Biosystems, pp. 1-50 (2002).*
Letter/Written Disclosure of the Information Disclosure Statement for the above-referenced application, filed herewith on Jul. 5, 2016, 2 pages.
Letter/Written Disclosure of the Information Disclosure Statement for the above-referenced application, mailed Apr. 1, 2015, 2 pages.
Aline et al., "Toxoplasma gondii antigen-pulsed-dendritic cell-derived exosomes induce a protective immune response against T. gondii infection." Infect Immun. 72:4127-4137 (2004).
Beauvillain et al. "A vaccine based on exosomes secreted by a dendritic cell line confers protection against T. gondii infection in syngeneic and allogeneic mice." Microbes Infect 9:1614-1622 (2007).
Chirgwin et al., "Isolation of biologically active ribonucleic acid from sources enriched in ribonuclease." Biochemistry, 18(24):5294-5299 (1979).
Chomczynski, P. and N. Saachi, "Single-step method of RNA isolation by acid guanidinium thiocyanate-phenol-chloroform extraction." Analytical Biochemistry 162(1):156-159 (1987).

(Continued)

*Primary Examiner* — Teresa E Strzelecka
(74) *Attorney, Agent, or Firm* — Knobbe, Martens, Olson & Bear LLP

(57) ABSTRACT

The present invention relates to a method of enriching for membranous microvesicles relative to the cellular population in a biological sample. More particularly, there is provided a method for enriching for exosomes from plasma. In a related aspect, there is provided a method of reducing the concentration of cellular and cellular derived molecules in a biological sample. Still further, the present invention provides methods for selectively isolating mRNA subpopulations from exosomes. Yet further, there are provided methods of amplifying exosome derived RNA. The method of the present invention is useful in a range of applications including, but not limited to, diagnostic, prognostic, therapeutic, research and development applications, to the extent that the enrichment of exosomes is required.

20 Claims, 8 Drawing Sheets
(1 of 8 Drawing Sheet(s) Filed in Color)
Specification includes a Sequence Listing.

(56) References Cited

OTHER PUBLICATIONS

Colino, J. and C. Snapper, "Dendritic cell-derived exosomes express a *Streptococcus pneumoniae* capsular polysaccharide type 14 cross-reactive antigen that induces protective immunoglobulin responses against pneumococcal infection in mice," Infect Immun 75:220-230 (2007).

Delcayre, A. and J. Le Pecq, "Exosomes as novel therapeutic nanodevices," Curr Opin Mol Ther 8:31-38 (2006).

Delcayre et al., "Exosome Display technology: applications to the development of new diagnostics and therapeutics." Blood Cells Mol Dis 35:158-168 (2005).

Hao et al., "Dendritic cell-derived exosomes stimulate stronger CD8+ CTL responses and antitumor immunity than tumor cell-derived exosomes." Cell Mol Immunol 3:205-211 (2006).

Hao et al., "Mature dendritic cells pulsed with exosomes stimulate efficient cytotoxic T-lymphocyte responses and antitumour immunity." Immunology 120:90-102 (2007).

Hong et al., "Colorectal cancer cell-derived microvesicles are enriched in cell cycle-related mRNAs that promote proliferation of endothelial cells." BMC Genomics 10:556, 13 pages (2009).

Hoorn et al., "Prospects for urinary proteomics: exosomes as a source of urinary biomarkers," Nephrology (Carlton) 10:283-290 (2005).

Keller et al., "Exosomes: from biogenesis and secretion to biological function." Immunol. Lett. 107(2): 102-108 (2006).

Kim et al., "MHC class II+ exosomes in plasma suppress inflammation in an antigen-specific and Fas ligand/Fas-dependent manner." J Immunol. 179:2235-2241 (2007).

Kuate et al., "Exosomal vaccines containing the S protein of the SARS coronavirus induce high levels of neutralizing antibodies." Virology 362:26-37 (2007).

Lopez, R., "Pneumococcus: the sugar-coated bacteria." Int Microbiol 9:179-190 (2006).

Makwana, N. and F. Riordan, "Bacterial meningitis: the impact of vaccination." CNS Drugs 21:355-366 (2007).

Pisitkun et al., "Discovery of urinary biomarkers," Mol Cell Proteomics 5:1760-1771 (2006).

Pisitkun et al., "Identification and proteomic profiling of exosomes in human urine." Proc Natl Acad Sci 101:13368-13373 (2004).

QIAamp Circulating Nucleic Acid Handbook, May 2009 <available at http://www.qiagen.com/resources/download.aspx?id=0c4b3lab-f4fb-425f-99bf-10ab9538c061&lang=en>, [accessed Jul. 23, 2014] 56 pages.

Wolfers et al. "Tumor-derived exosomes are a source of shared tumor rejection antigens for CTL cross-priming." Nat Med 7:297-303 (2001).

Zitvogel et al., "Eradication of established murine tumors using a novel cell-free vaccine: dendritic cell-derived exosomes." Nat Med 4:594-600 (1998).

Written Opinion, dated Dec. 7, 2011, in connection with International Patent Application No. PCT/AU2011/001371, 6 pages.

International Search Report, dated Dec. 12, 2011, in connection with International Patent Application No. PCT/AU2011/001371, 6 pages.

International Preliminary Report on Patentability, dated Apr. 29, 2014, in connection with International Patent Application No. PCT/AU2011/001371, 7 pages.

Letter/Written Disclosure of the Supplemental Information Disclosure Statement for the above-referenced appliction, filed herewith on Sep. 29, 2017, 2 pages.

DeFrancesco, L., "Ode to Oligo(dT): Oligo(dT) Takes on a Variety of Faces in Kits for the Purification of mRNA," The Scientist, 7 pages (1998).

Examination Report, dated Feb. 16, 2017, in connection with corresponding Australian Patent Application No. 2011320021, 3 pages.

Tsui et al., Clin Chem, 2002, 48:10.

\* cited by examiner

FIGURE 1

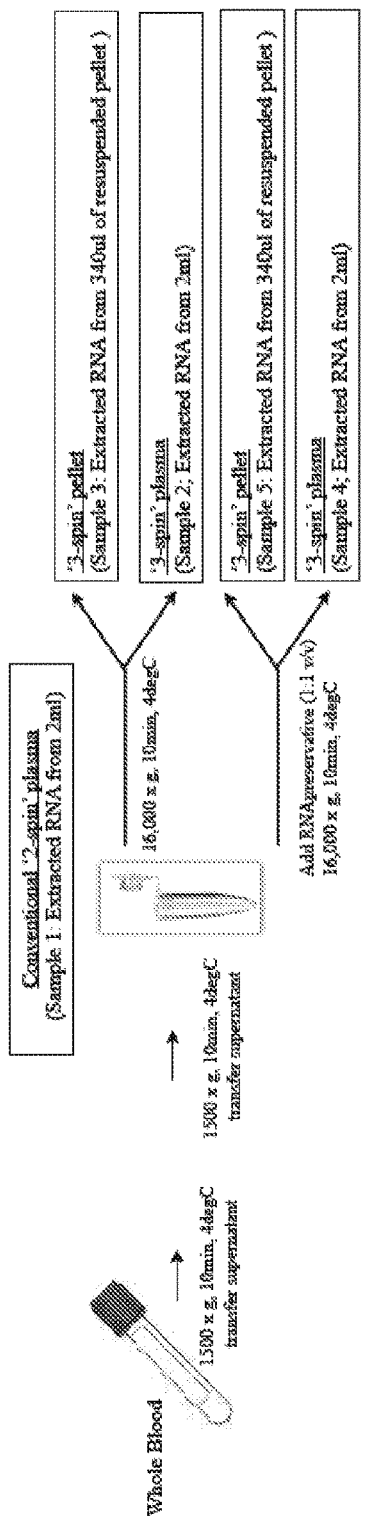

Table 1: Measurement of GAPDH mRNA in plasma and pellet samples

| Sample | Resulting RNA* volume (ul) | GAPDH RNA copies in 1.25ul RNA** | Volume correction factor*** | Total GAPDH RNA copies per ml original samples | % GAPDH relative to Sample 1 |
|---|---|---|---|---|---|
| '2-spin plasma' (sample 1) | 100 | 3,880 | x80 | 155,200 | 100% |
| '3-spin plasma' (sample 2) | 100 | 117 | x80 | 4,680 | 3% |
| '3-spin pellet' (sample 3) | 10 | 6,650 | x8 | 26,600 | 17.1% |
| Introduction of a third 16,000g spin resulted in a total loss of ~80% of the original GAPDH mRNA '2-spin' plasma signal | | | | | |
| 3-spin plasma' w/preservative (sample 4) | 100 | 1,903 | x80 | 152,240 | 98.1% |
| 3-spin pellet' w/preservative (sample 5) | 10 | 0.1 | x8 | 0.8 | — |
| Addition of RNA preservation result in 98.1% recovery of the original signal. | | | | | |

* RNA was extracted from plasma using the QIAamp® "isolation of circulating nucleic acids from plasma/sera" as described by manufacturer (QIAGEN®). RNA was converted to cDNA using the Invitrogen®'s VILO cDNA transcription kit as recommended by manufacturer.
** Quantitative real-time PCR was performed on 2.5ul cDNA in 25ul PCR setups using Invitrogen® qPCR Express Supermix as recommended together with GAPDH forward primer, GAA GGT GAA GGT CGG AGT (SEQ ID NO:1), GADH reverse primer, GAA GAT GGT GAT GGG ATTTC (SEQ ID NO: 2) and a dual-labelled hydrolysis probe 5'-(FAM) CAA GCT TCC CGT TCT CAG CC (TAMRA)-3' (SEQ ID NO: 3). The GAPDH copies were calculated using a GAPDH standard curve with known copies of GAPDH per PCR reaction (Figure 2).
*** Measurements were done on 1.25ul RNA aliquots.

Figure 2. GAPDH RNA qPCR standard curve

Figure 3. DAPI-staining based examination of the 18,000g generated pellet

*No intact cell nuclei were detectable*

SEQUENCE LISTING

<160> NUMBER OF SEQ ID NOS: 9

<210> SEQ ID NO 1
<211> LENGTH: 18
<212> TYPE: DNA
<213> ORGANISM: artificial
<220> FEATURE:
<223> OTHER INFORMATION: PCR primer

<400> SEQUENCE: 1
gaaggtgaag gtcggagt                                                  18

<210> SEQ ID NO 2
<211> LENGTH: 20
<212> TYPE: DNA
<213> ORGANISM: artificial
<220> FEATURE:
<223> OTHER INFORMATION: PCR primer

<400> SEQUENCE: 2
gaagatggtg atgggatttc                                                20

<210> SEQ ID NO 3
<211> LENGTH: 20
<212> TYPE: DNA
<213> ORGANISM: artificial
<220> FEATURE:
<223> OTHER INFORMATION: PCR primer

<400> SEQUENCE: 3
caagcttccc gttctcagcc                                                20

<210> SEQ ID NO 4
<211> LENGTH: 23
<212> TYPE: DNA
<213> ORGANISM: artificial
<220> FEATURE:
<223> OTHER INFORMATION: PCR primer

<400> SEQUENCE: 4
gaatgcggct aatcccaacc tcg                                            23

<210> SEQ ID NO 5
<211> LENGTH: 23
<212> TYPE: DNA
<213> ORGANISM: artificial
<220> FEATURE:
<223> OTHER INFORMATION: PCR primer

<400> SEQUENCE: 5
ggaaacacgg acacccaaag tag                                            23

<210> SEQ ID NO 6
<211> LENGTH: 25
<212> TYPE: DNA
<213> ORGANISM: artificial
<220> FEATURE:
<223> OTHER INFORMATION: PCR primer

<400> SEQUENCE: 6
tgcgcgttac gacaggccaa tcact                                          25

<210> SEQ ID NO 7
<211> LENGTH: 19
<212> TYPE: DNA
<213> ORGANISM: artificial

```
<220> FEATURE:
<223> OTHER INFORMATION: PCR primer

<400> SEQUENCE: 7
gaactcgcca tctggctca                                              19

<210> SEQ ID NO 8
<211> LENGTH: 19
<212> TYPE: DNA
<213> ORGANISM: artificial
<220> FEATURE:
<223> OTHER INFORMATION: PCR primer

<400> SEQUENCE: 8
gggtagcaga gccccactc                                              19

<210> SEQ ID NO 9
<211> LENGTH: 27
<212> TYPE: DNA
<213> ORGANISM: artificial
<220> FEATURE:
<223> OTHER INFORMATION: PCR primer

<400> SEQUENCE: 9
tcaacttcaa caagggcgac tggatcc                                     27
```

METHOD OF MICROVESICLE ENRICHMENT

RELATED APPLICATIONS

This application is the National Stage of International Application. No. PCT/AU2011/001371, filed 26 Oct. 2011, the specification of which is incorporated by reference herein.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Apr. 22, 2014, is 2 kilobytes in size, and titled 801SEQUS1.txt.

FIELD OF THE INVENTION

The present invention relates to a method of enriching for membranous microvesicles relative to the cellular population in a biological sample. More particularly, there is provided a method for enriching for exosomes from plasma. In a related aspect, there is provided a method of reducing the concentration of cellular and cellular derived molecules in a biological sample. Still further, the present invention provides methods for selectively isolating mRNA subpopulations from exosomes. Yet further, there are provided methods of amplifying exosome derived RNA. The method of the present invention is useful in a range of applications including, but not limited to, diagnostic, prognostic, therapeutic, research and development applications, to the extent that the enrichment of exosomes is required.

BACKGROUND OF THE INVENTION

Bibliographic details of the publications referred to by author in this specification are collected alphabetically at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Exosomes are 30-100 nm vesicles secreted by a wide range of mammalian cell types (Keller et al. (2006). *Immunol. Lett.* 107(2): 102-8). An exosome is created intracellularly when a segment of the cell membrane invaginates and is endocytosed (Keller et al. 2006 supra). The internalized segment is broken into smaller vesicles that are subsequently released or shed from the cell. The latter stage occurs when the late endosome, containing many small vesicles, fuses with the cell membrane, triggering the release of the vesicles from the cell. The vesicles (once released are called exosomes) consist of a lipid raft embedded with ligands common to the original cell membrane. Exosomes secreted by cells under normal and pathological conditions contain proteins and RNA molecules including mRNA and miRNA, which can be shuttled from one cell to another, affecting the recipient cell's protein production. However, of importance in the context of their therapeutic and diagnostic utility is the fact that they carry RNA and protein from the cell they were released from. Exosomes appear to lack DNA and possibly ribosomal RNA and contain mostly mRNA and miRNA.

In the late 1970's, tumour-derived exosomes were identified in the peripheral circulation of women with ovarian cancer. Since then, a range of cell types have been demonstrated to be capable of releasing exosomes, including reticulocytes, B cells, T cells, mast cells, epithelial cells and embryonic cells. Exosomes are reported to be secreted in increased amounts in a variety of biological fluids and can be enriched with certain RNA transcripts several hundred-fold compared to normal cells (Hong et al. 2009, *BMC Genomics* 10:556-569). Since plasma derived exosomes lack ribosomal RNA, RNA extracted from exosomes exhibits a higher proportion of transcripts specific to tumour cells, for example, that may even otherwise be below the detection limit in the tumour cells themselves.

Accordingly, since their discovery, a growing number of therapeutic and diagnostic applications have been developed, in particular in the context of neoplastic conditions. The use of exosomes has garnered considerable interest as vaccine candidates for tumor immunotherapy (Delcayre and Le Pecq, 2006, *Curr Opin Mol Ther* 8:31-38). Much of this interest stems from the difficulty associated with dendritic cell-based immunotherapy and how an exosome-based approach can overcome some of these difficulties. Tumor cell-derived exosomes containing tumor antigens plus MHC class 1 molecules can transfer tumor antigens to dendritic cells to induce a CD8+ T-cell dependent anti-tumor immune response (Hao et al. *Cell Mol Immunol* 2006; 3:205-211). Exosomes released from dendritic cells pulsed with tumor antigens were also shown to elicit strong anti-tumor responses. Data obtained in mice have shown that exosomes obtained from dendritic cells pulsed with tumor peptides could prime specific cytotoxic T lymphocytes (CTLs) in vivo and limit or suppress growth of established murine tumors in a T-cell-dependent manner (Zitvogel et al. *Nat Med* 1998; 4:594-600; Hao et al. *Immunology* 2007; 120: 90-102).

Interestingly, tumor-derived exosomes may have broader activity than previously believed as one study showed that exosomes isolated from different tumors inhibited not only syngeneic but also allogenic tumor growth, indicating that tumor-derived exosomes may harbor some common tumor antigens (Wolfers et al. *Nat Med* 2001; 7:297-303). Together, these studies indicate that exosomes can be recovered from tumor cells or from dendritic cells pulsed with tumor antigens to deliver a target immunogen capable of inducing an effective immune response and that they may represent a new cell-free vaccine.

The successful use of exosomes in cancer immunotherapy has also lead to the hypothesis that they could function as vaccine candidates in the context of infectious diseases. Aline et al. demonstrated that exosomes derived from dendritic cells pulsed with *T. gondii* tachyzoite sonicates could induce a protective immune response against *T. gondii* infection. These exosomes primed an antigen-specific cellular and humoral immune response, which provided a good protection against both acute and chronic toxoplasmosis (Aline et al. 2004, *Infect Immun.* 72:4127-4137). Moreover, CBA/J mice vaccinated with exosomes isolated from *T. gondii* antigen-pulsed dendritic cells exhibited significantly fewer brain cyst (Beauvillain et al. 2007, *Microbes Infect* 9:1614-1622).

Another application of exosomes in immunotherapy has been implicated in the treatment of pneumococcal infection in mice (Colino et al. 2007, *Infect Immun* 75:220-230). Colino and Snapper showed that murine bone marrowderived dendritic cells (BMDCs) pulsed in vitro with intact diphtheria toxin (DT)-released exosomes, which upon injection into mice induce immunoglobulin G (IgG)2b and IgG2a responses specific for DT (Colino et al 2007, supra). Exosomes have also been evaluated in the context of *Streptococcus* infections. Invasive strains of *Streptococcus pneumoniae* are leading causes of meningitis and major causes of otitis media and bacteremia in children and pneumonia in the elderly (Lopez, 2006, *Int Microbiol* 9:179-190). Vaccine-mediated protection against *S. pneumoniae* infection is based on humoral immunity specific for *S. pneumoniae* capsular polysaccharides (Cps) (Makwana et al. *CNS Drugs* 2007, 21:355-366). Similar to the DT exosomes, BMDCs treated with Cps14 released exosomes enriched in Cps14. These purified exosomes could induce a *S. pneumoniae*-protective Cps14-specific immunoglobulin M and IgG3 response in naive recipients (Colino et al. 2007, supra).

Exosomes as a vaccine has also been explored for atypical severe acute respiratory syndrome (SARS) caused by the positive-stranded RNA virus, SARS-associated cornavirus (SARS-CoV). Studies by Kuate et al. showed that exosomes containing spike S protein of SARS-CoV induced neutralizing antibody titres (Kuate et al. 2007, *Virology* 362:26-37). This immune response was further accentuated by priming with the SARS-S exosomal vaccine and then boosting with the currently used adenoviral vector vaccine (Kuate et al. 2007, supra).

In addition to the potential use of exosomes as vaccines against infectious diseases, exosomes have also proved useful in treatment of autoimmune diseases in animal models. This is illustrated in studies by Kim et al. who showed that administration of exosomes derived from dendritic cells-expressing recombinant IL-4 was able to modulate the activity of APC and T cells in vivo, partly through a FasL/Fas-dependent mechanism, resulting in effective treatment against collagen-induced arthritis through suppression of the delayed-type hypersensitivity inflammatory response (Kim et al. 2007, *J Immunol.* 179:2235-2241).

Exosome display technology is a novel technique of manipulating the molecular composition of the exosomes and tailoring exosomes with new desirable properties. Recently, exosome display was applied for the induction of epitope-specific antibody response against tumor biomarkers (Delcayre et al. *Blood Cells Mol Dis* 2005, 35:158-168). This technology opens up new possibilities in designing novel therapies and generating new diagnostic tools. Exosome display has been used to prepare recombinant vesicles carrying cytokines as well as tumor antigens that may or may not have been previously found on exosomes (Delcayre et al. 2006 supra). The targeted co-delivery of antigens with the activators of dendritic cells, B-, T- or natural killer cells may also improve the efficacy of exosome-based vaccines.

In terms of diagnostics, the proteins associated with renal diseases could be detected on exosomes isolated from urine, indicating a possible use for urine exosomes as biomarkers (Pisitkun et al. 2006, *Mol Cell Proteomics* 5:1760-1771). For instance, Pisitkun et al. demonstrated the excretion of exosomes containing aquaporin-2 protein in autosomal dominant and autosomal recessive nephrogenic diabetes insipidus patients (Pisitkun et al. *Proc Natl Acad Sci USA* 2004, 101:13368-13373). Similar proteomic studies performed on urinary exosomes generated a long list of molecular signatures, illustrating valuable potential for diagnostic, prognostic and pathophysiological discovery (Hoorn et al, 2005, *Nephrology* (Carlton); 10:283-290).

Similarly to renal pathologies, exosomes are also an attractive source of biomarker candidates for cancer diagnosis including, for example bladder cancer. The differentially expressed proteins found in exosomes include psoriasin, keratin-14, galectin-7, epidermal fatty acid binding protein (E-FABP), migration inhibitor factor-related protein (MRP8) and 14 and stratifin, which may be useful markers for the diagnosis of bladder cancer (Pisitkun et al. 2006, *Mol Cell Proteomics* 5:1760-1771).

Exosomes may also be valuable as biomarkers or as a source of biomarkers for infectious diseases, for example in the context of defining treatment success. Exosomes may be particularly useful in the context of tuberculosis (TB) as the time required to test a new TB drug treatment protocol is extensive, leading to high drug development cost as well as delays in the introduction of new medication. A major limitation in developing an efficient drug treatment for TB is the lack of available methodology to identify an early infection as well as to determine drug treatment efficacy. Currently, a major goal of TB research is to identify disease biomarkers in biological fluids that can be measured relatively inexpensively for early diagnosis of disease and treatment monitoring.

It has therefore become increasingly clear, as new exosome studies are published, that these small bioactive membranous microvesicles are important in a wide range of biological functions. From their original discovery in the removal of unwanted proteins from maturing reticulocytes to their role in immune surveillance, the inventory of functions continues to grow. As cancer phase I clinical trials have shown, the knowledge of exosomes can be applied therapeutically and the use of exosomes in diagnostics is also likely to grow. However, the absence of standardised and specific methods of exosome recovery as well as exosome-specific quality control methods to maximise the purity of recovered exosome populations has been a significant limitation to furthering the use of exosomes both therapeutically and diagnostically. Current approaches are centred on capturing or enriching for exosomes from plasma using antibody-based capture (targeting exosome specific surface antigens), ultracentrifugation (i.e. centrifugation speed>60,000 g) or filtration. Both immunocapture and ultracentrifugation based isolation of exosomes require advanced equipment instruments and highly skilled staff. Hence these technologies are not readily implemented at clinical sites. Other methods for purifying exosomes are based on two sequential spins of a biological fluid, such as plasma, at 1,600 g each. However, detection and measurement of nucleic acids derived from circulating exosomes requires complete elimination of haematopoietic cells as their cellular. RNA content otherwise may affect the specificity of PCR-based detection of biomarkers of interest. To date, the methods which have been utilised have not achieved particularly good enrichment or purification of exosomes, particularly to the extent that these methods aim to recover and analyse exosome-derived RNA, the result of which is of limited value if contaminating cellular RNA is not removed. Accordingly, there is an ongoing need to develop better methods for isolating exosomes, in particular from plasma.

In work leading up to the present invention it has been determined that a significantly improved level of membranous microvesicle purity in a biological sample, relative to a contaminating cellular population, can be obtained if the biological sample is subjected to mechanical cellular rupture. This is achieved by virtue of the fact that the physical structure and characteristics, such as mass, of a membranous microvesicle have been determined to be sufficiently different from those of a cell that selective disruption of the membrane of a cell, but not a membranous microvesicle, can be achieved. The nucleic acid or proteinaceous material released from the cells is thereafter degraded by the actions of enzymes either naturally present or introduced to the biological sample. This effectively and simply clears the biological sample of non-microvesicle nucleic acid material, thereby achieving enrichment of the membranous microvesicles. Still further, in terms of conducting analysis of the membranous microvesicle-derived nucleic acid or protein material, there is no need to necessarily conduct any further purification or separation steps on the biological sample since the nucleic acid and protein component of the biological material is essentially only the nucleic acid or protein derived from the non-disrupted component of the specimen, that is, the membranous microvesicles. The technique described herein is extremely simple and effective, thereby enabling the enrichment of membranous microvesicles, such as exosomes, relative to a cellular population, from any biological sample, such as blood, plasma, lymph, saliva and urine, where the enriched membranous microvesicles which are obtained are intact and therefore suitable for application in any therapeutic, diagnostic, prognostic or other application.

To the extent that the enrichment of an exosome population is sought for the purpose of extracting and analysing the exosome mRNA, it has been further determined that exosome-derived mRNA does, in fact, comprise a poly(A) tail, thereby enabling very simple isolation of exosome mRNA via the specificity provided by the poly(A) tail. This enables isolation of the mRNA with minimal signal loss. mRNA isolation methods which have been used to date have generally been more complex in that they have been based on less specific means of isolating free nucleic acid molecules, such as silica columns.

Still further, methods of efficiently achieving the recovery and amplification of exosome RNA have been developed. The development of these methods now facilitates the routine recovery of more highly enriched populations of exosomes from a biological sample and further, the RNA contained therein. This has not previously been achievable at the level of simplicity and specificity now provided. The method of the present invention is useful in a range of diagnostic, therapeutic, research and development applications.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

One aspect of the present invention is directed to a method of enriching for membranous microvesicles in a biological sample, said method comprising subjecting said biological sample to mechanical cellular rupture, wherein said mechanical cellular rupture selectively ruptures cells but not membranous microvesicles.

In another aspect there is provided a method of enriching for exosomes in a biological sample, said method comprising subjecting said biological sample to mechanical cellular rupture, wherein said mechanical cellular rupture selectively ruptures cells but not exosomes.

In still another aspect the present invention is directed to a method of enriching for exosomes in a blood, serum, plasma, saliva, urine or stool, said method comprising subjecting said blood, serum, plasma, saliva, urine or stool sample to mechanical cellular rupture, wherein said mechanical cellular rupture selectively ruptures cells but not exosomes.

In yet another aspect there is provided a method of enriching for exosomes in a biological sample, said method comprising subjecting said sample to centrifugation, wherein said centrifugation selectively ruptures cells but not exosomes.

In still yet another aspect there is provided a method of enriching for exosomes in a biological sample, said method comprising subjecting said sample to bead milling, wherein said bead milling selectively ruptures cells but not exosomes.

In yet still another aspect there is provided a method of enriching for membranous microvesicles in a biological sample, said method comprising subjecting said sample to centrifugation at 15,000-17,000 g.

In a further aspect there is provided a method of enriching for membranous microvesicles in a biological sample, said method comprising subjecting said sample to centrifugation at 15,000 g-17,000 g at 2° C.-9° C.

In another further aspect there is provided a method of enriching for membranous microvesicles in a biological sample, said method comprising subjecting said sample to centrifugation at about 16,000 g at about 4° C.

In yet another further aspect there is provided a method of enriching for membranous microvesicles in a biological sample, said method comprising subjecting said sample to centrifugation for about 10 minutes at about 16,000 g at about 4° C.

In still a further aspect there is provided a method of enriching for membranous microvesicles in a biological sample, said method comprising the steps of:
(i) subjecting said biological sample to centrifugation at 1,000 g-2,000 g;
(ii) subjecting the supernatant obtained in accordance with step (i) to centrifugation at 1,000 g-2,000 g; and
(iii) subjecting the supernatant obtained in accordance with step (ii) to centrifugation at 15,000 g-17,000 g.

In yet another aspect there is provided a method of enriching for membranous microvesicles in a biological sample, said method comprising the steps of:
(i) subjecting said biological sample to centrifugation at 1,000 g-2,000 g at 2° C.-9° C.;
(ii) subjecting the supernatant obtained in accordance with step (i) to centrifugation at 1,000 g-2,000 g at 2° C.-9° C.; and
(iii) subjecting the supernatant obtained in accordance with step (ii) to centrifugation at 15,000 g-17,000 g at 2° C.-9° C.

In still another aspect there is provided a method of enriching for membranous microvesicles in a biological sample, said method comprising the steps of:
(i) subjecting said biological sample to centrifugation at about 1,500 g at about 4° C.;

(ii) subjecting the supernatant obtained in accordance with step (i) to centrifugation at about 1,500 g at about 4° C.; and
(iii) subjecting the supernatant obtained in accordance with step (ii) to centrifugation at about 16,000 g at about 4° C.

In still yet another aspect there is provided a method of enriching for membranous microvesicles in a biological sample, said method comprising the steps of:
(i) subjecting said biological sample to centrifugation for about 10 minutes at about 1,500 g at about 4° C.;
(ii) subjecting the supernatant obtained in accordance with step (i) to centrifugation for about 10 minutes at about 1,500 g at about 4° C.; and
(iii) subjecting the supernatant obtained in accordance with step (ii) to centrifugation for about 10 minutes at about 16,000 g at about 4° C.

In still another aspect there is provided a method for enriching for membranous microvesicles in a biological sample, said method comprising subjecting said sample to bead milling wherein said bead is about 0.1 mm-0.5 mm in diameter.

In accordance with this aspect there is provided a method for enriching for membranous microvesicles in a biological sample, said method comprising subjecting said sample to bead milling at about 20-40 Hz for about 2-5 minutes and wherein said bead is about 0.1 mm-0.5 mm in diameter.

In a related aspect of the present invention provides a method for enriching for membranous microvesicle nucleic acid and/or protein molecules in a biological sample, said method comprising:
(i) subjecting said biological sample to mechanical cellular rupture wherein said mechanical cellular rupture selectively ruptures cells but not exosomes;
(ii) contacting the sample of step (i) with a nucleic acid and/or protein degradation enzyme for a time and under conditions sufficient to degrade free nucleic acid and/or protein molecules;
(iii) neutralising the enzymes of step (ii); and
(iv) lysing the exosomes in the sample of step (iii) to release their nucleic acid and protein content.

In another aspect there is provided a method of enriching for exosomal nucleic acid and/or protein molecules in a biological sample, said method comprising the steps of:
(i) subjecting said biological sample to centrifugation at 1,000 g-2,000 g;
(ii) subjecting the supernatant obtained in accordance with step (i) to centrifugation at 1,000 g-2,000 g;
(iii) subjecting the supernatant obtained in accordance with step (ii) to centrifugation at 15,000 g-17,000 g;
(iv) contacting the sample of step (iii) with a nucleic acid and/or protein degradation enzyme for a time and under conditions sufficient to degrade free nucleic acid and protein molecules;
(v) neutralising the enzymes of step (iv); and
(vi) lysing the exosomes in the sample of step (v) to release their nucleic acid and protein content.

In yet another aspect there is provided a method of enriching for exosomal nucleic acid and/or protein molecules in a biological sample, said method comprising the steps of:
(i) subjecting said biological sample to centrifugation at 1,000 g-2,000 g at 2° C.-9° C.;
(ii) subjecting the supernatant obtained in accordance with step (i) to centrifugation at 1,000 g-2,000 g at 2° C.-9° C.; and
(iii) subjecting the supernatant obtained in accordance with step (ii) to centrifugation at 15,000 g-17,000 g at 2° C.-9° C.;
(iv) contacting the sample of step (iii) with a nucleic acid and/or protein degradation enzyme for a time and under conditions sufficient to degrade free nucleic acid and protein molecules;
(v) neutralising the enzymes of step (iv); and
(vi) lysing the exosomes in the sample of step (v) to release their nucleic acid and protein content.

In still another aspect there is provided a method of enriching for exosomal nucleic acid and/or protein molecules in a biological sample, said method comprising the steps of:
(i) subjecting said biological sample to centrifugation at about 1,500 g at about 4° C.;
(ii) subjecting the supernatant obtained in accordance with step (i) to centrifugation at about 1,500 g at about 4° C.; and
(iii) subjecting the supernatant obtained in accordance with step (ii) to centrifugation at about 16,000 g at about 4° C.;
(iv) contacting the sample of step (iii) with a nucleic acid and/or protein degradation enzyme for a time and under conditions sufficient to degrade free nucleic acid and protein molecules;
(v) neutralising the enzymes of step (iv); and
(vi) lysing the exosomes in the sample of step (v) to release their nucleic acid and protein content.

In still yet another aspect there is provided a method of enriching for exosomal nucleic acid and/or protein molecules in a biological sample, said method comprising the steps of:
(i) subjecting said biological sample to centrifugation for about 10 minutes at about 1,500 g at about 4° C.;
(ii) subjecting the supernatant obtained in accordance with step (i) to centrifugation for about 10 minutes at about 1,500 g at about 4° C.; and
(iii) subjecting the supernatant obtained in accordance with step (ii) to centrifugation for about 10 minutes at about 16,000 g at about 4° C.;
(iv) contacting the sample of step (iii) with a nucleic acid and/or protein degradation enzyme for a time and under conditions sufficient to degrade free nucleic acid and protein molecules;
(v) neutralising the enzymes of step (iv); and
(vi) lysing the exosomes in the sample of step (v) to release their nucleic acid and protein content.

In still another aspect there is provided a method of enriching for exosomal nucleic acid and/or protein molecules in a biological sample, said method comprising the steps of:
(i) subjecting said biological sample to bead milling;
(ii) contacting the sample of step (i) with a nucleic acid and/or protein degradation enzyme for a time and under conditions sufficient to degrade free nucleic acid and protein molecules;
(iii) neutralising the enzymes of step (ii); and
(iv) lysing the exosomes in the sample of step (iii) to release their nucleic acid and protein content.

In a further aspect there is provided a method of enriching for exosomal nucleic acid and/or protein molecules in a biological sample, said method comprising the steps of:
(i) subjecting said biological sample to bead milling at about 20-40 Hz for about 2-5 minutes and wherein said bead is about 0.1-0.5 mm in diameter;
(ii) contacting the sample of step (i) with a nucleic acid and/or protein degradation enzyme for a time and under conditions sufficient to degrade free nucleic acid and protein molecules;

(iii) neutralising the enzymes of step (ii); and
(iv) lysing the exosomes in the sample of step (iii) to release their nucleic acid and protein content.

A related aspect of the present invention is directed to a method of reducing the concentration of cells and cellular-derived molecules in a biological sample, said method comprising subjecting said biological sample to mechanical cellular rupture wherein said mechanical cellular rupture selectively ruptures cells but not membranous microvesicles.

In another aspect there is provided a method of isolating exosome-derived mRNA from a biological sample, said method comprising the steps of:
(i) subjecting said biological sample to mechanical cellular rupture wherein said mechanical cellular rupture selectively ruptures cells but not exosomes;
(ii) contacting the sample of step (i) with RNA degradation enzymes for a time and under conditions sufficient to degrade free nucleic acid molecules;
(iii) neutralising the enzymes of step (ii);
(iv) lysing the exosomes in the sample of step (iii) to release their nucleic acid content; and
(v) isolating the polyadenylated RNA.

In yet another aspect of the present invention there is provided a method of obtaining amplified membranous microvesicle RNA from a biological sample, said method comprising the steps of:
(i) subjecting said biological sample to mechanical cellular rupture wherein said mechanical cellular rupture selectively ruptures cells but not exosomes;
(ii) contacting the sample of step (i) with an RNA degradation enzyme for a time and under conditions sufficient to degrade free RNA;
(iii) lysing the exosomes obtained in accordance with step (ii);
(iv) isolating the polyadenylated RNA using oligo(dT) affinity chromatography; and
(v) amplifying the RNA of step (iv).

In a further aspect there is provided a method of obtaining amplified exosomal RNA of interest from a biological sample, said method comprising the steps of:
(i) subjecting the biological sample to centrifugation at 15,000 g-17,000 g;
(ii) contacting the sample of step (i) with an RNA degradation enzyme for a time and under conditions sufficient to degrade free RNA;
(iii) lysing the exosomes obtained in accordance with step (ii);
(iv) isolating the polyadenylated RNA using oligo(dT) affinity chromatography; and
(v) amplifying the RNA step of (vi) using a 1-step or 2-step RT-PCR.

In another aspect there is provided a method of obtaining amplified exosomal RNA of interest from a biological sample, said method comprising the steps of:
(i) subjecting the biological sample to bead milling;
(ii) contacting the sample of step (i) with an RNA degradation enzyme for a time and under conditions sufficient to degrade free RNA;
(iii) isolating the polyadenylated RNA using oligo(dT) affinity chromatography; and
(iv) amplifying the RNA of step (iii) using a 1-step or 2-step RT-PCR.

In yet another aspect of the present invention, there is provided a method of obtaining amplified membranous microvesicle mRNA from a biological sample, said method comprising the steps of:
(i) subjecting said biological sample to mechanical cellular rupture wherein said mechanical cellular rupture selectively ruptures cells but not exosomes;
(ii) contacting the sample of step (i) with an RNA degradation enzyme for a time and under conditions sufficient to degrade free RNA;
(iii) isolating the RNA using the QIAAMP® circulating nucleic acid kit protocol but wherein:
 (a) the ACW2 butter wash step of the QIAAMP® silica column is performed twice;
 (b) the ethanol wash step of the QIAAMP® silica column is performed twice;
 (c) the RNA is eluted in a final volume of about 35 μl;
 (d) the eluate of step (c) and AVE buffer are reapplied to the column; and
(iv) amplifying the RNA of step (iii).

In a further aspect the present invention provides a method of obtaining amplified exosome mRNA from a biological sample, said method comprising the steps of:
(i) subjecting the biological sample to either centrifugation at 15,000 g-17,000 g or bead milling;
(ii) contacting the sample of step (i) with an RNA degradation enzyme for a time and under conditions sufficient to degrade free RNA;
(iii) isolating the RNA using the QIAmp circulating nucleic acid kit protocol but wherein:
 (a) the ACW2 butter wash step of the QIAmp silica column is performed twice;
 (b) the ethanol wash step of the QIAmp silica column is performed twice;
 (c) the RNA is eluted in a final volume of about 35 μl;
 (d) the eluate of step (c) and AVE buffer are reapplied to the column; and
(iv) amplifying the RNA of step (iii) by RT-PCR.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1. Plasma and pellet generation work flow.

DETAILED DESCRIPTION OF THE INVENTION

Figure 2:
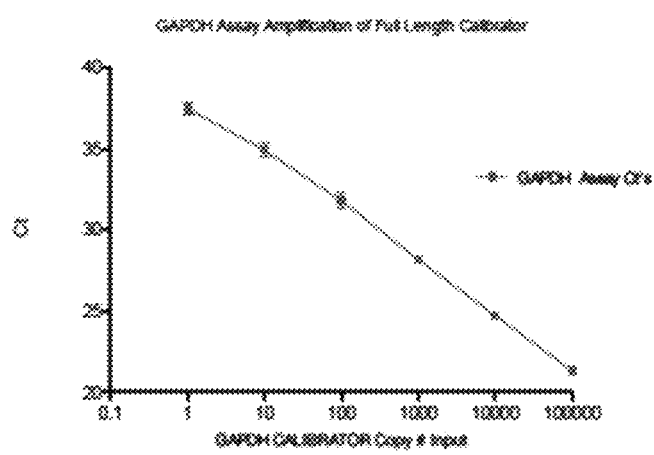
FIG. 2. GAPDH RNA qPCR standard curve.

The present invention is predicated, in part, on the determination that the distinct physical characteristics of cells, such as mass, relative to membranous microvesicles, such as exosomes, facilitate the application of a mechanical cellular rupture step to selectively rupture the cellular component of a biological sample, leaving the membranous microvesicles intact. The action, in the biological sample, of enzymes which degrade nucleic acid and protein material thereby leads to selective degradation of cellular DNA, or RNA and/or protein, which enables enrichment of membranous microvesicle nucleic acid or protein without the need to apply any further separation steps. Still further, the determination that the RNA contained within exosomes, in particular, comprises a poly(A) tail has enabled the development of routine yet highly efficient means of isolating this RNA based on the specific targeting of the poly(A) tail. These findings have also enabled the design of more effective protocols, than are currently available, for achieving the isolation and amplification of exosome derived RNA.

Accordingly, one aspect of the present invention is directed to a method of enriching for membranous microvesicles in a biological sample, said method comprising subjecting said biological sample to mechanical cellular rupture, wherein said mechanical cellular rupture selectively ruptures cells but not membranous microvesicles.

Reference to "membranous microvesicle" should be understood as a reference to any particle which is comprised of a cellular plasma membrane component. Said membranous microvesicles may adopt a structure which takes the form of a lumen surrounded by plasma membrane. Examples of membranous microvesicles include, but are not limited to, microparticles, exosomes, apoptotic blebs, apoptotic bodies, cellular blebs and the like. In one embodiment, said membranous microvesicles are exosomes.

According to this embodiment, there is provided a method of enriching for exosomes in a biological sample, said method comprising subjecting said biological sample to mechanical cellular rupture, wherein said mechanical cellular rupture selectively ruptures cells but not exosomes.

Reference to "exosome" should be understood as a reference to the vesicles which are secreted by, a wide variety of cell types. Without limiting the present invention to any one theory or mode of action, late endosomes or multivesicular bodies contain intralumenal vesicles which are formed by the inward budding and scission of vesicles from the limited endosomal membrane into these enclosed nanovesicles. These intralumenal vesicles are then released from the multivesicular body lumen into the extracellular environment during exocytosis upon fusion with the plasma membrane. An exosome is created intracellularly when a segment of membrane invaginates and is endocytosed. The internalised segments which are broken into smaller vesicles and ultimately expelled from the cell contain proteins and RNA molecules such as mRNA and miRNA. Since plasma-derived exosomes largely lack ribosomal RNA, they are a useful and accurate indication of the mRNA levels of genes of interest in the context of the cells from which these exosomes have been secreted, such as neoplastic cells.

The exosomes of the present invention are enriched from a biological sample. By "biological sample" is meant any biological material derived from a plant, animal, microorganism (such as a prokaryotic organism) or a parasite. Such samples include, but are not limited to, blood, serum, plasma, urine, lymph, cerebrospinal fluid, ascites, saliva, mucus, stool, biopsy specimens, breast milk, gastric juice, pleural fluid, semen, sweat, tears, vaginal secretion and fluid which has been introduced into the body of an animal and subsequently removed such as, for example, the saline solution extracted from the lung following lung lavage or the solution retrieved from an enema wash. The biological sample which is tested according to the method of the present invention may be tested directly or may require some form of pre-treatment prior to testing. For example, the sample may require the addition of a reagent, such as a buffer, to mobilise the sample. It should be further understood that the sample which is the subject of testing may be freshly isolated or it may have been isolated at an earlier point in time and subsequently stored or otherwise treated prior to testing. For example, the sample may have been collected at an earlier point in time and frozen or otherwise preserved in order to facilitate its transportation to the site of testing. In yet another example, the sample may be treated to neutralise any possible pathogenic infection, thereby reducing the risk of transmission of the infection to the technician.

In one embodiment, said biological sample is a blood, serum, plasma, saliva, urine or stool.

According to this embodiment, the present invention is directed to a method of enriching for exosomes in a blood, serum, plasma, saliva, urine or stool, said method comprising subjecting said blood, serum, plasma, saliva, urine or stool sample to mechanical cellular rupture, wherein said mechanical cellular rupture selectively ruptures cells but not exosomes.

To the extent that the subject biological sample is harvested from an animal, the term "animal" should be understood to include a human, primate, livestock animal (e.g. sheep, pig, cow, horse, donkey), laboratory test animal (e.g. mouse, rat, rabbit, guinea pig), companion animal (e.g. dog, cat), captive wild animal (e.g. fox, kangaroo, deer), ayes (e.g. chicken, geese, duck, emu, ostrich), reptile or fish. Preferably, the subject animal is a human.

Reference to "mechanical cellular rupture" should be understood as a reference to any technique which achieves the breaking open of a cell by the destruction of its wall or membrane. As hereinbefore described, due to differences in the physical characteristics of cells relative to membranous microvesicles, mechanical cellular rupture methods can be designed such that they exhibit sufficient force to disrupt a cell but not a membranous microvesicle. This is due to the significant difference in physical characteristics such as the relatively larger mass of cells relative to microvesicles. Since methods for examining a biological sample to identify the presence of intact cells or membranous microvesicles are extremely simple and routine, means for optimising any of the widely known standard techniques for mechanical cell rupture, to ensure that exosomes are not also ruptured, is a matter of routine procedure. Similarly, optimising any newly developed techniques would also be straightforward.

Methods of achieving mechanical cellular rupture are well known in the art and include, but are not limited to:
(i) centrifugation
(ii) sonication (with or without the inclusion of surfactants)
(iii) bead milling with or without the addition of surfactants using, for example, small glass, ceramic, zirconium or steel beads
(iv) homogenization
(v) nitrogen burst method
(vi) small probe ultrasound
(vii) hypotonic shock
(viii) High-shear mechanical methods;

(ix) rotor-stator disruptors,
(x) valve-type processors,
(xi) fixed geometry processors,
(xii) constant pressure processors,
(xiii) osmosis based electroporation, and
(xiv) electropermeabilization As detailed hereinbefore, with methods of examining a biological sample to identify intact cells and exosomes being extremely well known, and in light of the disclosures provided herein, the optimisation of these techniques to facilitate rupture of cell membranes but not exosome membranes is facilitated. In one embodiment, said mechanical cell rupture technique is centrifugation or bead milling which selectively disrupts fluid components based on size and shape differences.

Accordingly, there is provided a method of enriching for exosomes in a biological sample, said method comprising subjecting said sample to centrifugation, wherein said centrifugation selectively ruptures cells but not exosomes.

In another embodiment, there is provided a method of enriching for exosomes in a biological sample, said method comprising subjecting said sample to bead milling, wherein said bead milling selectively ruptures cells but not exosomes.

In accordance with these embodiments, said biological sample is blood, serum, plasma, saliva, urine or stool.

That the physical characteristics of exosomes, relative to cells, are sufficiently distinct to facilitate routine and reliable selective membrane rupture was not previously recognised in terms of providing a means to effect enrichment. Accordingly, prior art methods of purifying exosomes have always focussed on density based separation techniques, filtration or membrane antigen-specific affinity isolation of exosomes. However, as shown by the data provided herein, a standard density based separation technique does not clear a biological sample of cellular material. Depending on the purpose for which the exosome population is sought, this level of cellular contamination can be problematic. The method of the present invention therefore provides a means for enriching intact exosomes.

Reference to "enriching" should be understood as a reference to increasing the proportion of membranous microvesicles in a biological sample relative to the intact cellular population of said sample. As detailed hereinbefore, this is performed without the need to necessarily employ any preliminary or subsequent separation steps. This is a significant improvement relative to prior art methods which are based on the application of a preliminary step to remove contaminants, such as cells, from the sample. However, it should be understood that since the biological sample need not necessarily (although this is not excluded) be subjected to any other purification or isolation step, the exosome population is not necessarily purified. As would be appreciated, mechanical rupture of the cellular population, although reducing the level of intact cells in the sample, does leave the ruptured cell membrane and released cytosolic molecules in the biological sample. For many applications, however, this will not be problematic and means that the enrichment method can be performed as a single step procedure which does not require the application of any separation steps, such as separation of a centrifuged pellet from the supernatant. To the extent that a pure exosome population is required, further separation steps can be performed, as deemed necessary.

It should also be understood that depending on the specific application of the method of the invention, samples may not be tested in advance to determine whether or not they contain an exosome population. That is, the method of the present invention may simply be applied as a matter of routine procedure to enrich an exosome population, if it is present. Irrespective of whether or not there are exosomes present in the sample, performing this method on a biological sample for the purpose of enriching such a population, should it be present, or even to merely determine whether exosomes are present or not, should be understood to fall within the scope of the present invention.

In a related aspect, it has been determined that to the extent that the subject biological sample is a blood or plasma sample, or any other biological sample which either naturally or otherwise contains enzymes which degrade a molecule of diagnostic interest e.g. nucleic acids and/or proteins, the method of the present invention will achieve enrichment of the exosome population relative to not only the cellular population but, also, relative to the non-microvesicle proteinaceous and non-proteinaceous material in that sample.

Non-microvesicle proteinaceous and non-proteinaceous material should be understood as material which is not contained within, or otherwise forms part of, an intact membranous microvesicle. Such non-microvesicle material includes, but is not limited to, cells, proteins, RNA, DNA or other cell debris which has been released from a cell due to apoptosis, cell death or cell lysis, for example. It should therefore still be understood that the method of the present invention, although significantly more efficient in removing cellular and nucleic acid contaminants from a biological sample than prior art methods, may not necessarily enrich the membranous microvesicle preparation to the point of complete purity, although depending on the nature of the starting material this outcome should not be excluded. As exemplified herein, the method of the present invention achieves a 97% improvement in plasma sample exosome purity relative to the traditional two spin prior art methods. As detailed hereinbefore, one of the problems with the prior art methods for purifying exosomes is that they are not particularly efficient. Accordingly, significant cellular material can remain as a contaminant in the sample to be tested, thereby potentially skewing the results of analyses such as RNA expression profiling, particularly where exosome expression levels may be swamped by normal cellular levels, thereby effectively leading to masking of the results.

The method of the present invention is directed to overcoming the fact that the conventionally used method of two spins at 1,500 g-1,600 g, although removing a substantial portion of contaminating cellular material, does not remove all of it. Sufficient contamination remains to negatively impact on the utility of exosomes and other membranous microvesicles as a diagnostic tool. In fact, this has been one of the major limitations to furthering the use of exosomes diagnostically and therapeutically. The development of the present invention is predicated on the determination that a mechanical rupture process can be selectively directed to the cellular component of a biological sample while maintaining the integrity of the exosomes, thereby significantly improving the removal of cellular contamination in a single step process. Although the ruptured cellular material remains in solution, for many applications this is not problematic. In other situations, it provides a convenient point at which to purify the exosome population based on separating proteinaceous and non-proteinaceous debris from the intact exosome population. However, to the extent that the sample is one which inherently contains nucleases and/or proteinases, such as plasma, the nucleic acid and/or protein component of, these disrupted contaminants will be degraded, but not that of the nucleic acids and proteins within the intact exosome. If one is seeking to amplify or sequence exosome nucleic acid material, for example, there will not be a need to further purify the subject biological sample since techniques directed to analysing nucleic acid material are selective in this regard and provided that non-exosome nucleic acid material has been degraded, accurate results will be obtained. This is significant since it has been shown that prior art cell depleted plasma may contain contaminating cells and cellular debris. The method developed and described herein has been determined to achieve both removal of unwanted cellular material without damaging exosome structure and, further, achieving degradation of contaminating nucleic acid molecules, prior to analysis of the exosome-derived nucleic acids. Without limiting the present invention to any one theory or mode of action, it is thought that the nucleases which are naturally present in biological samples, such as plasma, act to naturally degrade contaminating extracellular nucleic acid, in particular RNA.

To the extent that in one embodiment the mechanical cell rupture step is performed using centrifugation, reference to "centrifugation" should be understood as a reference to the process of applying centrifugal force to a sample. Although in its standard application this method uses the application of centrifugal force to separate components within a sample based on density, in the context of the present invention it is designed to selectively rupture cells, rather than just pushing them into a pellet and then decanting/harvesting the supernatant which contains the exosomes. In fact, this latter method is the typical prior art method which does require separation of the supernatant from the pellet since the cells in the pellet would not expect to be ruptured and would retain their nucleic acid content. Still further, it has been determined that at prior art speeds, not all cells are removed from the supernatant. Accordingly, even if the supernatant is separated from the pellet, it will still contain contaminating cells which retain their nucleic acid content. That being the case, if the purpose of harvesting the exosome population is to analyse its RNA, for example, this will necessarily lead to aberrant results since all the steps designed to preserve and harvest the exosome RNA would equally preserve and harvest the RNA of the intact cells remaining in solution. However, by applying the method of the present invention, all cells are lysed and therefore the exosome population is heavily enriched as a population of membranous vesicles. It is therefore not necessary to separate the supernatant from any pellet which may have formed since any such pellet will not be comprised of whole cells. Such an additional separation step would therefore be superfluous.

Even to the extent that it is sought to analyse the exosomal RNA, the fact that the exosomes remain in solution with degraded cellular material is of little consequence since the newly exposed cellular nucleic acid will be degraded by enzymes either naturally present in, or added to, the biological sample. Accordingly, for many applications, no further enrichment or purification need be performed other than the single step method of the present invention. It should be understood, however, that this does not exclude the performance of any additional steps. For example, one might want to perform one or two spins to pellet out and remove a proportion of the most dense particulate material present in the sample and to thereafter perform the method of the invention on the supernatant harvested therefrom. However, the unique advantage of the method of the invention is that this is not, in fact, necessary. Nevertheless, it is well within the skill of the person of skill in the art to determine both what type of sample to use and the nature of its mode of preparation prior to application of the present method and, further, how to treat the enriched exosome population subsequently to its enrichment.

Accordingly, in one embodiment there is provided a method of enriching for membranous microvesicles in a biological sample, said method comprising subjecting said sample to centrifugation at 15,000-17,000 g.

In another embodiment, said membranous microvesicles are exosomes.

In still another embodiment, said biological sample is blood, serum, plasma, saliva, urine or stool.

In yet another embodiment, the centrifugation is conducted at a low temperature, such as 2° C.-10° C., preferably, about 3° C., 4° C., 5° C., 6° C., 7° C., 8° C. or 9° C. in order to maintain exosome viability. However, although it is common laboratory practice to conduct centrifugation at low temperatures, it should be understood that this aspect of the method of the invention can be conducted at any temperature up to room temperature.

According to this embodiment there is therefore provided a method of enriching for membranous microvesicles in a biological sample, said method comprising subjecting said sample to centrifugation at 15,000 g-17,000 g at 2° C.-9° C.

In another embodiment, said centrifugation is performed at about 3° C., 4° C., 5° C., 6° C., 7° C. or 8° C. In yet another embodiment, said centrifugation is performed at about 4° C.

In another embodiment, said membranous microvesicles are exosomes.

Reference to the centrifugation being performed at "about" a specified centrifugal force should be understood as a reference to the fact that the recited centrifugal force need not be exactly that amount but may be approximately that amount. Reference hereinbefore to "about" in the context of the temperature at which the method should be performed should be understood to have a corresponding meaning. The centrifugation is performed at 15,000 g-17,000 g, preferably about 15,000 g, 15,050 g, 15,100 g, 15,150 g, 15,200 g, 15,250 g, 15,300 g, 15,350 g, 15,400 g, 15,450 g, 15,500 g, 15,550 g, 15,600 g, 15,650 g, 15,700 g, 15,750 g, 15,800 g, 15,850 g, 15,900 g, 15,950 g, 16,000 g, 16,050 g, 16,100 g, 16,150 g, 16,200 g, 16,250 g, 16,300 g, 16,350 g, 16,400 g, 16,450 g, 16,500 g, 16,550 g, 16,600 g, 16,650 g, 16,700 g, 16,750 g, 16,800 g, 16,850 g, 16,900 g, 16,950 g or 17,000 g. In one particular embodiment, said centrifugation is performed at 15,500 g-16,500 g and even more particularly at about 16,000 g.

According to this embodiment, there is provided a method of enriching for membranous microvesicles in a biological sample, said method comprising subjecting said sample to centrifugation at about 16,000 g at about 4° C.

In another embodiment, said membranous microvesicles are exosomes.

The centrifugation step of the method of the present invention is performed for such time as is required to rupture the membranes of the cellular material which is present in the sample. In this regard, centrifugation for approximately 10 minutes can achieve this outcome. As detailed hereinbefore, reference to centrifugation for "about" 10 minutes should be understood to mean approximately 10 minutes and not necessarily precisely 10 minutes. Without limiting the present invention to any one theory or mode of action, it would be understood by the person of skill in the art that the centrifugation outcome of rupturing the membranes of the subject cellular material can be achieved provided that the sample is spun for a sufficient minimum time to force disruption of the cell membrane. This may be achievable with a centrifugation time of less than 10 minutes. Still further, centrifugation for longer than 10 minutes is unlikely to be problematic since once the cellular material has been ruptured, any further centrifugation will simply maintain this status but will not otherwise rupture the membranes of the exosomes unless the force was increased. Still further, although it is preferable that the centrifugation step is performed as a single, continuous spin, it would also be possible to achieve the same outcome even if the spin was stopped and then restarted. Accordingly, the present invention should be understood to extend to this type of routine adaptation of the basic method.

In yet another embodiment, there is therefore provided a method of enriching for membranous microvesicles in a biological sample, said method comprising subjecting said sample to centrifugation for about 10 minutes at about 16,000 g at about 4° C.

In one embodiment said membranous microvesicle is an exosome.

In another embodiment, said biological sample is a blood, serum, plasma, urine, stool, ascites, cerebrospinal fluid or saliva sample.

In yet another embodiment, said biological sample is a human biological sample.

In still another embodiment, the biological sample of the present invention is subjected to an initial crude enrichment for the membranous microvesicle population of a biological sample. For example, said crude enrichment may be performed via preliminary centrifugation.

According to this embodiment there is provided a method of enriching for membranous microvesicles in a biological sample, said method comprising the steps of:
(i) subjecting said biological sample to centrifugation at 1,000 g-2,000 g;
(ii) subjecting the supernatant obtained in accordance with step (i) to centrifugation at 1,000 g-2,000 g; and
(iii) subjecting the supernatant obtained in accordance with step (ii) to centrifugation at 15,000 g-17,000 g.

In yet another embodiment there is provided a method of enriching for membranous microvesicles in a biological sample, said method comprising the steps of:
(i) subjecting said biological sample to centrifugation at 1,000 g-2,000 g at 2° C.-9° C.;
(ii) subjecting the supernatant obtained in accordance with step (i) to centrifugation at 1,000 g-2,000 g at 2° C.-9° C.; and
(iii) subjecting the supernatant obtained in accordance with step (ii) to centrifugation at 15,000 g-17,000 g at 2° C.-9° C.

In still another embodiment, there is provided a method of enriching for membranous microvesicles in a biological sample, said method comprising the steps of:
(i) subjecting said biological sample to centrifugation at about 1,500 g at about 4° C.;
(ii) subjecting the supernatant obtained in accordance with step (i) to centrifugation at about 1,500 g at about 4° C.; and
(iii) subjecting the supernatant obtained in accordance with step (ii) to centrifugation at about 16,000 g at about 4° C.

In still yet another embodiment, there is provided a method of enriching for membranous microvesicles in a biological sample, said method comprising the steps of:
(i) subjecting said biological sample to centrifugation for about 10 minutes at about 1,500 g at about 4° C.;
(ii) subjecting the supernatant obtained in accordance with step (i) to centrifugation for about 10 minutes at about 1,500 g at about 4° C.; and
(iii) subjecting the supernatant obtained in accordance with step (ii) to centrifugation for about 10 minutes at about 16,000 g at about 4° C.

According to these embodiments, the membranous microvesicles may be exosomes.

In a further embodiment, the biological sample may be blood, serum, plasma, urine, stool, ascites, cerebrospinal fluid or saliva.

Following the centrifugation of step (i), the supernatant remaining thereafter is typically harvested and subjected to the centrifugation of step (ii). By "harvesting" is meant that the supernatant is separated from the pelleted material which forms during the centrifugation process. This can be done by any suitable means such as aspiration or decanting of the aqueous phase. A corresponding process is performed in the context of the supernatant which remains subsequently to the centrifugation of step (ii). That is, it is separated from the pellet which formed during the centrifugation process and is then subjected to the centrifugation of step (iii).

In still another embodiment, there is provided a method for enriching for membranous microvesicles in a biological sample, said method comprising subjecting said sample to bead milling wherein said bead is about 0.1 mm-0.5 mm in diameter.

In one embodiment said membranous microvesicle is an exosome.

In another embodiment, said biological sample is a blood, serum, plasma, urine, stool, ascites, cerebrospinal fluid or saliva sample.

In still another embodiment said sample is bead milled at approximately 20-40 Hz, preferably about 30 Hz, for 2-5 minutes.

In accordance with this embodiment there is provided a method for enriching for membranous microvesicles in a biological sample, said method comprising subjecting said sample to bead milling at about 20-40 Hz for about 2-5 minutes and wherein said bead is about 0.1 mm-0.5 mm in diameter.

Reference to "bead milling" should be understood as a reference to the method of disrupting cells and tissues by rapid agitation in the presence of small particles. Generally, the cells are agitated in suspension. The particles ("beads") may be made of any suitable material, such as glass. The cells break, to release intracellular molecules, because of shear forces, grinding between beads and collision with beads.

In another embodiment, said bead milling is performed at about 30 Hz and said beads are glass beads.

In still another embodiment, said bead milling is preceded by an initial crude enrichment step, such as an initial centrifugation step.

As described hereinbefore, the supernatant which may be harvested subsequently to the crude enrichment centrifugation of steps (i) and (ii) detailed earlier will comprise any molecules present in the biological sample which are of a density insufficient to be pelleted out of solution at the given centrifugal force. Without limiting the present invention in any way, it is expected that intact exosomes and any non-degraded nucleic acid or protein material which has been released from dying or damaged cells would remain in solution. However, cells (such as haematopoietic cells in blood samples together with some larger cell fragments) may be pelleted and therefore effectively separated out and discarded as a result of the process of centrifugation and harvesting of the supernatant using these initial crude centrifugation steps. However, the advantage of the present method is that any such initial crude separation step is not essential and is therefore entirely optional. If one does elect to perform this type of preliminary centrifugation, it would be appreciated that this can be done prior to any selected mechanical disruption technique. For example, one may perform a preliminary centrifugation step before performing the bead milling step. However, as detailed above, it would be appreciated that such preliminary steps are not essential and the advantage of the method of the present invention is not only that it provides a much better level of microvesicle enrichment than prior art methods but also that the method is much simpler to perform in that it does not require multiple centrifugation steps such as the prior art methods.

As detailed hereinbefore it should be understood that subsequently to mechanical cellular rupturing, there may still be left in solution some contaminants (i.e., non-exosome molecules). To the extent that these contaminants are nucleic acid molecules, such as DNA and RNA, they can be conveniently removed (if this is deemed necessary by virtue of the particular application which is envisaged for the enriched exosomes). Similarly, proteins can also be removed. This can be achieved via the use of enzymes such as nucleases and proteases. Provided that the exosomes themselves have not been lysed for the purpose of accessing their nucleic acid or protein content, this provides a convenient means of further enriching the sample which is obtained by the method of the present invention. To this end, and without limiting the present invention in any way, it has been observed that in at least plasma samples, there are sufficient endogenous ribonucleases present to degrade free RNA, such as cytosolic derived RNA released due to breakage of contaminating cells subsequently to the mechanical rupturing step, during the process of the present invention. Since this method has been designed to ensure that the integrity of the exosomes, although not the cells, is maintained, to the extent that the RNA contained within the exosomes is of ultimate interest, this provides a convenient means to remove contaminating free RNA such that the results obtained from analysis of the exosomal derived RNA are accurate. It should be understood that if insufficient amounts of functional nucleases (DNAses or ribonucleases) or proteinases are naturally present in the sample, these molecules can be introduced into the sample at any suitable time point, such as prior to commencement of the mechanical cellular rupture process or part way through. Similarly, the method of the present invention should be understood to also encompass other similar forms of routine adaptation to suit a particular application. To the extent that the enriched exosomes are sought to be used for a purpose such as therapeutic administration, the presence of minor soluble contaminants, such as free nucleic acids, proteins or cell membrane debris, may not be problematic.

It should be understood that reference herein to "nucleic acid or protein degradation enzyme" is a reference to any enzyme which acts to degrade DNA, RNA or protein. With respect to nucleic acid degradation enzymes, many enzymes are specific in that they act on one type of nucleic acid or the other. However, there are enzymes which act on both. An example of a nucleic acid degradation enzyme is a nuclease. A nuclease is generally understood as an enzyme which cleaves the phosphodiester bonds between nucleotide subunits of nucleic acids. Examples of nucleases include DNases (deoxyribonucleases) and RNases (ribonucleases). Numerous types of DNase and RNase have been isolated and characterized. They differ among other things in substrate specificity, cofactor requirements, and whether they cleave nucleic acids internally (endonucleases), digest the nucleic acid molecule from the ends (exonucleases) or attack in both of these modes. In many cases, the substrate specificity of a nuclease depends upon the concentration of enzyme used in the reaction, with high concentrations promoting less specific cleavages. The most widely used nucleases are DNase I and RNase A, both of which are purified from bovine pancreas:

(i) Deoxyribonuclease I cleaves double-stranded or single stranded DNA. Cleavage preferentially occurs adjacent to pyrimidine (C or T) residues, and the enzyme is therefore an endonuclease. Major products are 5'-phosphorylated di, tri and tetranucleotides. In the presence of magnesium ions, DNase I hydrolyzes each strand of duplex DNA independently, generating random cleavages. In the presence of manganese ions, the enzyme cleaves both strands of DNA at approximately the same site, producing blunt ends or fragments with 1-2 base overhangs. DNase I does not cleave RNA, but crude preparations of the enzyme are contaminated with RNase A; RNase-free DNase I is readily available.

(ii) Ribonuclease A is an endoribonuclease that cleaves single-stranded RNA at the 3' end of pyrimidine residues. It degrades the RNA into 3'-phosphorylated mononucleotides and oligonucleotides. A number of other nucleases that are used to manipulate DNA and RNA are exonuclease III (*E. coli*), mung bean nuclease (mung bean sprouts), nuclease BAL 31 (*Alteromonas*), nuclease S1 (*Aspergillus*), ribonuclease T1 (*Aspergillus*).

To the extent that one chooses to add a nuclease to the subject sample, it is within the skill of the person in the art to determine what nuclease to use. If nucleases are naturally present in the sample, such as in a plasma sample, this may not be required. It should be understood that these methods apply equally in the context of using proteases or any other type of enzyme or agent which is designed to modulate the structure or functionality of one or more molecules which may be present in the sample.

The development of the method of the present invention now facilitates the routine yet highly efficient enrichment, from a biological sample, of the membranous microvesicle population and, in particular, the exosome population. As detailed hereinbefore, in some situations the method of the present invention may be performed to determine whether or not an exosome population is even present in the sample, particularly where it might only be present in low concentrations which might not otherwise be detectable in the absence of the application of this method. The membranous microvesicles which are enriched in accordance with the present invention are useful in a range of applications which include both using the membranous microvesicle itself, such as an exosome, for therapeutic purposes which centre on retaining its integrity or, alternatively, lysing the membranous microvesicle to access its internal nucleic acid or protein material. In the context of this latter example, analysing RNA levels, for example, has been found to be useful in the context of diagnostic and prognostic applications, particularly in the context of neoplastic conditions.

It should therefore be understood that depending on the ultimate use for the membranous microvesicles which are enriched in accordance with the method of the present invention, the treated sample will undergo further manipulation or treatment as required in the context of the selected application.

Accordingly, a related aspect of the present invention provides a method for enriching for membranous microvesicle nucleic acid and/or protein molecules in a biological sample, said method comprising:

(i) subjecting said biological sample to mechanical cellular rupture wherein said mechanical cellular rupture selectively ruptures cells but not exosomes;
(ii) contacting the sample of step (i) with a nucleic acid and/or protein degradation enzyme for a time and under conditions sufficient to degrade free nucleic acid and/or protein molecules;
(iii) neutralising the enzymes of step (ii); and
(iv) lysing the exosomes in the sample of step (iii) to release their nucleic acid and protein content.

In one embodiment, said nucleic acid molecules are RNA.

In another embodiment, said membranous microvesicle is an exosome.

In still another embodiment, said biological sample is blood, serum, plasma, saliva, urine or stool.

It would be appreciated that to the extent that RNA is sought to be harvested from plasma or other blood-derived samples, there is likely to be present sufficient endogenous nucleases to effect step (ii). However, to the extent that this is not the case, the requisite enzymes can be introduced prior, during or subsequently to step (i).

Reference to "free" nucleic acid molecules should be understood as a reference to nucleic acid molecules which are found in the biological sample but are not contained within a plasma membrane, exosome or a cell. These nucleic acid molecules may be derived from any source. However, their common feature is that they are not localised within a membranous structure and are therefore susceptible to degradation by nucleases present in the sample.

In yet another embodiment, said mechanical cellular rupture is effected via centrifugation.

In still another embodiment, said centrifugation is performed at 15,000 g-17,000 g, preferably at 2° C.-9° C., most preferably at about 4° C.

In a further embodiment, said centrifugation is performed at about 16,000 g, preferably for about 10 minutes.

In yet another embodiment, the biological sample of the present invention is subjected to an initial crude enrichment for the membranous microvesicle population of the biological sample, such as an initial centrifugation step.

According to one embodiment there is therefore provided a method of enriching for exosomal nucleic acid and/or protein molecules in a biological sample, said method comprising the steps of:
(i) subjecting said biological sample to centrifugation at 1,000 g-2,000 g;
(ii) subjecting the supernatant obtained in accordance with step (i) to centrifugation at 1,000 g-2,000 g;
(iii) subjecting the supernatant obtained in accordance with step (ii) to centrifugation at 15,000 g-17,000 g;
(iv) contacting the sample of step (iii) with a nucleic acid and/or protein degradation enzyme for a time and under conditions sufficient to degrade free nucleic acid and protein molecules;
(v) neutralising the enzymes of step (iv); and
(vi) lysing the exosomes in the sample of step (v) to release their nucleic acid and protein content.

In yet another embodiment there is provided a method of enriching for exosomal nucleic acid and/or protein molecules in a biological sample, said method comprising the steps of:
(i) subjecting said biological sample to centrifugation at 1,000 g-2,000 g at 2° C.-9° C.;
(ii) subjecting the supernatant obtained in accordance with step (i) to centrifugation at 1,000 g-2,000 g at 2° C.-9° C.; and
(iii) subjecting the supernatant obtained in accordance with step (ii) to centrifugation at 15,000 g-17,000 g at 2° C.-9° C.;
(iv) contacting the sample of step (iii) with a nucleic acid and/or protein degradation enzyme for a time and under conditions sufficient to degrade free nucleic acid and protein molecules;
(v) neutralising the enzymes of step (iv); and
(vi) lysing the exosomes in the sample of step (v) to release their nucleic acid and protein content.

In still another embodiment, there is provided a method of enriching for exosomal nucleic acid and/or protein molecules in a biological sample, said method comprising the steps of:
(i) subjecting said biological sample to centrifugation at about 1,500 g at about 4° C.;
(ii) subjecting the supernatant obtained in accordance with step (i) to centrifugation at about 1,500 g at about 4° C.; and
(iii) subjecting the supernatant obtained in accordance with step (ii) to centrifugation at about 16,000 g at about 4° C.;
(iv) contacting the sample of step (iii) with a nucleic acid and/or protein degradation enzyme for a time and under conditions sufficient to degrade free nucleic acid and protein molecules;
(v) neutralising the enzymes of step (iv); and
(vi) lysing the exosomes in the sample of step (v) to release their nucleic acid and protein content.

In still yet another embodiment, there is provided a method of enriching for exosomal nucleic acid and/or protein molecules in a biological sample, said method comprising the steps of:
(i) subjecting said biological sample to centrifugation for about 10 minutes at about 1,500 g at about 4° C.;
(ii) subjecting the supernatant obtained in accordance with step (i) to centrifugation for about 10 minutes at about 1,500 g at about 4° C.; and
(iii) subjecting the supernatant obtained in accordance with step (ii) to centrifugation for about 10 minutes at about 16,000 g at about 4° C.;
(iv) contacting the sample of step (iii) with a nucleic acid and/or protein degradation enzyme for a time and under conditions sufficient to degrade free nucleic acid and protein molecules;
(v) neutralising the enzymes of step (iv); and
(vi) lysing the exosomes in the sample of step (v) to release their nucleic acid and protein content.

In still another embodiment there is provided a method of enriching for exosomal nucleic acid and/or protein molecules in a biological sample, said method comprising the steps of:
(i) subjecting said biological sample to bead milling;
(ii) contacting the sample of step (i) with a nucleic acid and/or protein degradation enzyme for a time and under conditions sufficient to degrade free nucleic acid and protein molecules;
(iii) neutralising the enzymes of step (ii); and
(iv) lysing the exosomes in the sample of step (iii) to release their nucleic acid and protein content.

In a further embodiment there is provided a method of enriching for exosomal nucleic acid and/or protein molecules in a biological sample, said method comprising the steps of:
(i) subjecting said biological sample to bead milling at about 20-40 Hz for about 2-5 minutes and wherein said bead is about 0.1-0.5 mm in diameter;

(ii) contacting the sample of step (i) with a nucleic acid and/or protein degradation enzyme for a time and under conditions sufficient to degrade free nucleic acid and protein molecules;
(iii) neutralising the enzymes of step (ii); and
(iv) lysing the exosomes in the sample of step (iii) to release their nucleic acid and protein content.

In still another embodiment said bead milling is preceded by an initial crude enrichment step, such as an initial centrifugation step.

In a further embodiment, the biological sample may be blood, serum, plasma, saliva, urine or stool.

In still another embodiment said nucleic acid is RNA and said nucleic acid degradation enzyme is a ribonuclease.

A related aspect of the present invention is directed to a method of reducing the concentration of cells and cellular-derived molecules in a biological sample, said method comprising subjecting said biological sample to mechanical cellular rupture wherein said mechanical cellular rupture selectively ruptures cells but not membranous microvesicles.

In one embodiment, said mechanical cellular rupture is centrifugation.

In yet another embodiment, the centrifugation is conducted at a low temperature, such as 2° C.-10° C., preferably, about 3° C., 4° C., 5° C., 6° C., 7° C., 8° C. or 9° C.

In a further embodiment said centrifugation is performed at 15,000 g-17,000 g, preferably about 16,000 g.

In still another embodiment, said centrifugation is performed at about 4° C. for about 10 minutes.

In another embodiment, said biological sample is blood, serum, plasma, saliva, urine or stool.

In yet another embodiment, said mechanical cell rupture is bead milling.

In one embodiment, said bead is 0.1-0.5 mm in diameter.

In another embodiment, said sample is bead milled at approximately 20-40 Hz, preferably about 30 Hz, for 2-5 minutes.

In yet another embodiment, said beads are glass beads.

To the extent that it is sought to isolate and analyse the mRNA within the exosome, for example to assess changes to gene expression levels, it is necessary to lyse the exosome in order to expose its nucleic acid content and to thereafter analyse the mRNA subpopulation of nucleic acid molecules. Methods for isolating and analysing total RNA are well known. However, bearing in mind that total RNA comprises more than just mRNA, the specific analysis of mRNA can be compromised when it merely forms a smaller component of total RNA—particularly where the particular mRNA transcripts of interest are in very low copy number.

There are a wide variety of methods which can be and have been used to isolate total RNA from membranous microvesicles. The first step in isolating total RNA from such membranous microvesicles is to break open the vesicle under denaturing conditions. The methods which are utilised mirror the methods used to isolate RNA from cells. Chirgwin et al. *Biochemistry*, 18(24):5294-9, 1979) devised a method for the efficient isolation of total RNA by homogenization in a 4 M solution of the protein denaturant guanidinium thiocyanate with 0.1 M 2-mercaptoethanol to break protein disulfide bonds. Chirgwin then isolated RNA by ethanol extraction or by ultracentrifugation through cesium chloride. Chomezynski and Sacchi (*Analytical Biochemistry*, 162(1):156-9, 1987) modified this method to devise a rapid single-step extraction procedure using a mixture of guanidinium thiocyanate and phenol-chloroform, a method especially useful for processing large numbers of samples or for isolation of RNA from small quantities of cells or tissue.

Many of the kits currently available are based on these two methods, with proprietary mixes of guanidinium thiocyanate and phenol-chloroform for optimum results. However, these methods are not without drawbacks. Sedimentation of RNA by ultracentrifugation results in RNA pellets which can be difficult to resuspend, and organic extraction can lead to loss or fragmentation of RNA. If RNA is to be used in subsequent enzymatic reactions, salt residues resulting from use of guanidinium thiocyanate may interfere with results. In addition, methods employing guanidinium thiocyanate may result in poor RNA yields from plant tissue samples. Alternative lysis methods may therefore be used such as detergent lysis and organic extraction replaced with adsorption to an affinity matrix.

Access to isolated nucleic acids requires both cell lysis and inactivation of cellular nucleases, a process that must be harsh enough to break open cells, but gentle enough to result in intact nucleic acids. This may be achieved mechanically, by homogenization, or chemically, by detergent lysis or chaotropic agents. In most procedures, lysis and inactivation are achieved by a single solution. For example, TRIzol-TRIZOL® reagent, manufactured by Molecular Research Center Inc. and used in Life Technologies' MESSAGE-MAKER® mRNA Isolation System, is a mixture of acidic phenol and guanidine isothiocyanate. Tissue samples are lysed in TRIZOL®, and total RNA is obtained by chloroform extraction and isopropanol precipitation. Similarly, Chaosolv, used in ULTRASPEC® RNA isolation kits from BIOTECX Laboratories Inc., is a 14 M solution of guanidine salts and urea, which acts as a denaturing agent and is used in conjunction with phenol and other detergents.

For cells and tissue from which RNA is difficult to isolate by conventional methods, Bio101 offers the FastPrepFAST-PREP® System. This system is based on a benchtop instrument that uses a rapid reciprocating motion and a combination of matrices and chaotropic reagents to simultaneously homogenize tissue, lyse cells, and stabilize RNA in a matter of seconds. Rapid agitation of the lysing matrix leads to efficient lysis of a wide range of material. Each FASTRNA® kit, designed to isolate RNA from specific cell and tissue types, contains a different lysing matrix: silica particles (for bacteria), ceramic particles (for yeast, fungi, and algae), and zirconium particles (for plant and animal tissue).

Silica- or glass-based matrices or filters are popular choices for selective adsorption of RNA. Total RNA binds to the matrices or filters in the presence of chaotropic salts, usually enabling the user to avoid using organic solvents for extraction from lysates.

AMBION™ s RNAQUEOUS® systems rely on binding of RNA to a glass-fiber filter. In the standard RNAQUEOUS® kit, designed for small-scale applications, the filter is housed in a filter cartridge in a microfuge tube. Solutions are driven through the filter by centrifugation or under vacuum. For larger applications, the filter is housed in a luer lock syringe filter in the RNAQUEOUS®-MIDI kit. Solutions can be pushed through the glass-fiber filter using a 10- or 20-ml syringe. To process several samples at once, the syringe filter units can be fitted onto a vacuum manifold.

Bio101's RNaid® Plus kits include the proprietary silica gel-based RNAMATRIX®. Prior to binding RNA to the RNAMATRIX®, this protocol does require an acid phenol extraction of the lysate. RNA binding is in a batch format and the spin modules are used to separate eluted RNA from the matrix.

Using a reverse binding strategy, BIOLINE® Ltd.'s RNAce kits are used to isolate RNA from cell lysates by binding contaminating DNA to a mineral carrier. The resulting supernatant contains undegraded RNA that is free from contaminating DNA.

CLONTECH® offers NUCLEOSPIN® RNA II and NucleoTrap mRNA kits, both based on purification of RNA via a silica support. NUCLEOSPIN® columns contain a unique silica membrane that binds DNA and RNA in the presence of chaotropic salt. DNA is removed from the preparation by adding DNase I directly to the column. NucleoTrap is an activated spherical silica matrix in suspension that binds RNA.

S.N.A.P. is a silica-based resin available from INVITROGEN® Corp. In the S.N.A.P. Total RNA Isolation Kit, the resin comes in a membrane/column format, which allows for efficient multiple sample processing.

Life Technologies' GLASSMAX RNA Isolation Spin Cartridges contain a negatively charged silica matrix that binds RNA. Cells are lysed in guanidine isothiocyanate, and the sample suspended in an acid sodium solution. This is applied to the spin cartridges, from which bound RNA can then be eluted.

QIAGEN®'s RNEASY® kits combine the advantages of guanidinium thiocyanate lysis with rapid purification through a silica-gel membrane. To accommodate multiple applications, the membranes are housed in spin columns of various sizes and in 96-well plates. The RNEASY® 96 procedure can be performed manually using a vacuum manifold, a centrifuge, or automated on the BioRobot 9604. To increase RNA yield from plant tissue, QIAshredder columns are included in the RNEASY® Plant Mini Kit. These columns are used for homogenization and filtration of viscous plant and fungal lysates prior to use of the RNEASY® spin column.

ROCHE® Molecular Biochemicals' High Pure RNA isolation kits employ a glass-fiber fleece in a spin-filter tube to bind total nucleic acids. Copurified DNA is ultimately digested by a DNase I-digestion step. Kits are available for isolation of RNA from cultured cells, tissue, and viruses.

The StrataPrep Total RNA Miniprep kit isolates total RNA from a variety of tissues and cells from a wide range of sample quantities. Designed for experiments requiring small amounts of RNA, the protocol includes a specific DNA removal step that makes it ideal for preparing total RNA for RT-PCR. The microspin-cup format allows large numbers of samples to be processed simultaneously.

Magnetic separation offers a rapid means of separating RNA. Superparamagnetic particles, which can be made from a number of substances such as polystyrene or iron oxide and polysaccharides, are magnetic when placed in a magnetic field, but retain no residual magnetism when removed from the magnetic field. This lack of residual magnetism ensures that the particles can be repeatedly separated and resuspended without magnetically induced aggregation.

Magnetic particles can be used for a number of sorting applications such as immunosuppression, cell separation, and RNA/DNA separation. Molecules with specific biological affinities are attached to magnetic particles via functional groups that coat the particles. The moiety of interest binds to the attached molecule and the conjugated magnetic particle is removed from suspension by the application of a magnetic field. The RiboMag Total RNA Isolation Kit from ADVANCED BIOTECHNOLOGIES® combines magnetic separation and silica adsorption for the isolation of total RNA. Following a nonphenol lysis step and a quick spin to pellet cell walls, the supernatant is mixed with silica coated magnetic beads. For quantities over 10 μg, the magnetic separation can be substituted with alcohol precipitation. Magnetic separators are available for 10 or 20 1.5-ml tubes and 96-well plates. ADVANCED BIOTECHNOLOGIES® also offers a phenol guanidine-based Total RNA Isolation Reagent (TRIR), for single-step isolation of total RNA from tissues, cells, bacteria, plants, yeast, and biological fluids.

Nevertheless, the generality of these methods, in terms of their focus on extracting total RNA, is simply not ideal where subpopulations of mRNA are sought to be analysed. However, the general understanding in relation to exosome mRNA was that unlike newly transcribed mRNA, the transcripts found within an exosome were fragmented and degraded and no longer comprised a poly(A) tail.

In fact, however, in a related aspect of the present invention, it has been determined that exosome-derived mRNA is full length and polyadenylated. This unexpected finding has now enabled the development of methods of specifically isolating exosome mRNA based on targeting the poly(A) tail.

Accordingly, a related aspect of the present invention is directed to a method of isolating mRNA from an exosome-derived nucleic acid molecule population, said method comprising isolating polyadenylated RNA.

Reference to "nucleic acid molecule" should be understood as a reference to both DNA and RNA. In this regard, the subject RNA should be understood to encompass all forms of RNA including, but not limited to, primary RNA transcripts, mRNA, transfer RNA, miRNA and ribosomal RNA. The subject DNA and RNA may be intact or fragmented. It should be appreciated that the population of nucleic acid molecules which are targeted by the method of the present invention may be a pure population of nucleic acid molecules or an impure population. A typical example of an impure population is one in which not all non-nucleic acid material, such as cellular and exosomal membrane debris, have been removed. Although it is always desirable to work with as pure a population of nucleic acid molecules as possible, this is not always possible. Still further, the findings underpinning this aspect of the present invention in fact enable selective isolation of exosome-derived mRNA, irrespective of the nature of the content of the sample being tested.

That the subject nucleic acid molecule population is "exosome-derived" should be understood to mean that the nucleic acid molecules have been sourced from a population of exosomes. This can be achieved by any suitable method such as prior art methods or, preferably, the method of the present invention which has been found to provide a highly enriched population of exosomes from a biological sample.

According to this embodiment there is provided a method of isolating exosome-derived mRNA from a biological sample, said method comprising the steps of:
(i) subjecting said biological sample to mechanical cellular rupture wherein said mechanical cellular rupture selectively ruptures cells but not exosomes;
(ii) contacting the sample of step (i) with RNA degradation enzymes for a time and under conditions sufficient to degrade free nucleic acid molecules;
(iii) neutralising the enzymes of step (ii);
(iv) lysing the exosomes in the sample of step (iii) to release their nucleic acid content; and
(v) isolating the polyadenylated RNA.

In yet another embodiment, said mechanical cellular rupture is effected via centrifugation.

In still another embodiment, said centrifugation is performed at 15,000 g-17,000 g, preferably at 2° C.-9° C., most preferably at about 4° C.

In a further embodiment, said centrifugation is performed at about 16,000 g, preferably for about 10 minutes.

In still another embodiment, said mechanical cell rupture is effected via bead milling.

In one embodiment, said bead is 0.1-0.5 mm in diameter.

In another embodiment, said sample is bead milled at approximately 20-40 Hz, preferably about 30 Hz, for 2-5 minutes.

In yet another embodiment, said beads are glass beads.

In yet another embodiment, the biological sample of the present invention is subjected to an initial crude enrichment for the membranous microvesicle population of a biological sample, such as by centrifugation.

In a further embodiment, the biological sample may be blood, serum, plasma, urine, stool, ascites, cerebrospinal fluid or saliva.

In yet another embodiment, said biological sample is a human biological sample.

Reference to "lysing" the subject exosomes should be understood as a reference to rupturing the membrane of the exosome such that the content of the cytoplasm becomes exposed. This can be achieved by any suitable method. Since the exosome membrane is fundamentally similar to the cellular membrane, the methods which are widely used to lyse cells can be employed in the context of exosomes. For example, lysis can be achieved by either mechanical or chemical means. In either case, this is usually performed under denaturing conditions. For example, one might use homogenisation in the presence of the protein denaturant guanidine thiocyanate together with 2-mercaptoethanol to break protein disulfide bonds. Chemical means for inducing membrane lysis typically involve the use of detergents. It is well within the skill of the person in the art to select or design an appropriate method of lysing exosomes.

It should also be understood that subsequently to the lysis step, one may optionally enrich the RNA population prior to isolation of the polyadenylated RNA. Again, methods for achieving this are well known in the art and include, but are not limited to, ethanol extraction or ultracentrifugation through cesium chloride. Other methods which one might consider using include the single-step extraction procedure which uses a mixture of guanidine thiocyanate and phenol-chloroform. Organic extraction can also be replaced with adsorption to an affinity matrix, such as silica, if it is sought to enrich the total RNA population prior to isolation of mRNA. It is well within the skill of the person in the art to determine whether it is necessary to perform such an extraction and, if so, what method is best used.

Reference to "polyadenylated RNA" should be understood as a reference to RNA which comprises a poly(A) tail. Without limiting the present invention to any one theory or mode of action, polyadenylation is a covalent linkage of a polyadenylyl moiety to a messenger RNA molecule. In eukaryotic organisms, most messenger RNA molecules are polyadenylated at the 3' end. The poly(A) tail and the protein bound to it aid in protecting mRNA from degradation by exonucleases. Polyadenylation is also important for transcription termination, export of the mRNA from the nucleus, and translation. mRNA can also be polyadenylated in prokaryotic organisms, where poly(A) tails act to facilitate, rather than impede, exonucleolytic degradation. Polyadenylation occurs during and immediately after transcription of DNA into RNA. After transcription has been terminated, the mRNA chain is cleaved through the action of an endonuclease complex associated with RNA polymerase. After the mRNA has been cleaved, around 250 adenosine residues are added to the free 3' end at the cleavage site. This reaction is catalyzed by polyadenylated polymerase. Just as in alternative splicing, there can be more than one polyadenylation variant of an mRNA.

"Isolating" polyadenylated RNA can be achieved by any suitable method which targets and preferentially isolates RNA molecules which are polyadenylated. This is usually achieved by the application of some form of affinity binding which targets the poly(A) tail. Such methods are well known to those skilled in the art and can be performed as a matter of routine procedure.

Accordingly, in one embodiment said polyadenylated RNA is isolated with affinity chromatography.

For example, isolation of polyadenylated mRNA relies primarily on base-pairing between the poly(A)+ residues of the mRNA molecules and a synthetic chain of thymine residues (oligo [dT]n, where n denotes the number of T residues). Oligo (dT) cellulose is currently the most widely used matrix for mRNA isolation. The procedure can be carried out using batch binding and washing, whereby the matrix is suspended in solution, or by column chromatography. However, batch binding circumvents clogged columns and slow flow rates associated with column chromatography. Kits are available with prepacked columns for column chromatography, or with spin columns for elution of mRNA from batch-binding procedures.

QIAGEN®'s OLIGOTEX® Resin is an alternative to oligo (dT) cellulose. The resin is made up of dC10T30 oligonucleotides covalently linked to the surface of spherical polystyrene-latex particles (1.1-μm diameter). The large surface area and characteristics of the resin ensure rapid and efficient binding of poly(A)+mRNA, with greater than 90 percent recovery of mRNA consistently achieved. Magnetic separation of mRNA is also based on affinity-binding to oligo (dT). Magnetic particles coated with oligo (dT) are incubated with a cellular lysate or total RNA fraction. Because of the high surface-to-volume ratio of the beads, the mRNA rapidly binds to the oligo (dT). The magnetic beads are then isolated by placing the mixture in a magnetic field. This can be achieved by loading the cellular fraction onto a column on which the magnetic bead-mRNA complex is retained as long as the magnetic field is maintained. When the magnetic field is removed, the bound mRNA can be eluted from the beads.

An alternative separation strategy is to pellet the magnetic particles at the bottom of test tubes or microtiter plates. Magnetic separators, permanent magnets assembled to facilitate the different applications, are required for separation.

Magnetic particles are available in kits that include lysis and denaturing agents and elution and wash reagents, and in individual aliquots for a custom approach.

The large porous surface of the ultrapure iron oxide MegaCell for example, achieves a high level of binding of oligo (dT), resulting in efficient capture of mRNA. Separators are available from CORTEX® in both rack and block configurations to facilitate separation in a variety of receptacles.

Cruachem Inc.'s Isolate mRNA Pure Prep kit employs batch binding of oligo (dT) magnetic beads. Two magnetic separators are available: one for a single 2-ml microcentrifuge tube, and one for 10 2-ml microcentrifuge tubes.

MPG® mRNA purification kits are available from CPG Inc. MPG® consists of porous glass coated magnetic beads, which are coated with oligo (dT) for use in the mRNA purification kits. The beads are relatively large (5 µm in diameter) compared to some other available beads, but the porous surface of MPG® ensures a large surface area for binding and the size of the beads eliminates problems associated with separation of smaller particles.

DYNAL® offers DYNABEADS® Oligo (dT)25, polystyrene spheres coated with oligo (dT)25; the DYNABEADS® mRNA DIRECT Kit, for isolation of mRNA directly from cells, plants, or animal tissue; and the DYNABEADS® mRNA Purification Kit, for isolation of mRNA from total RNA. DYNABEADS® withstand heating and a wide range of pH and chemical treatments, and the uniformity of the polystyrene spheres ensures reproducible and predictable results. New protocols are available from DYNAL®, which combine DYNABEADS® coated with antibodies for cell isolation and DYNABEADS® coated with oligo (dT) for subsequent mRNA isolation, promising rapid and efficient isolation of cell-specific mRNA directly from complex biological samples.

MILTENYI® Biotec's MACS® MicroBeads, made of iron oxide and polysaccharide, are approximately 50 nm in diameter, similar to the size of a virus particle. Three kits are available: two for mRNA isolation from cells and tissues—both large and small scale—and one for mRNA isolation from total RNA. The mRNA is magnetically labelled by binding to oligo (dT) MACS® MicroBeads and isolated by passing the labelled mRNA and nonlabelled cellular components (or total RNA) over a separation column in the magnetic field of a MACS® separator.

MAGNETIGHT™ oligo (dT) particles are employed in NOVAGEN®'s Straight A's mRNA Isolation System. The coated magnetite beads are treated to minimize nonspecific interactions and can be used to isolate mRNA from a broad range of sources, including plant and animal tissues and cells, using the same protocol. After a single round of binding and elution from the MAGNETIGHT™ Oligo (dT) particles, mRNA is typically greater than 75 percent pure, compared with 50 percent pure after one round of binding to oligo (dT) cellulose. The speed and ease of use of magnetic particles ensure that a second round of recovery can be rapidly performed, resulting in significant reduction in rRNA contamination. The stability of the oligo (dT) covalent linkage and the low nonspecific binding properties of MAGNETIGHT™ Oligo (dT) particles make them ideally suited for repeated use.

Polysciences offers BIOMAG® Oligo (dT) particles and the BIOMAG® mRNA Purification Kit. Separation of magnetic particles in the purification kit is achieved by means of the Multi-6 Microcentrifuge Separator, which holds six 1.5-ml microcentrifuge tubes for separations of 20 to 500 µl.

PROMEGM®'s POLYATTRACT® mRNA isolation systems rely on biotin-streptavidin binding. In this system, mRNA binds to biotinylated oligo (dT) in solution. Bound mRNA is then immobilized by MAGNESPHERE® streptavidin-coated paramagnetic particles in a magnetic separation stand.

ROCHE® Molecular Biochemicals offers a similar system for mRNA isolation, whereby mRNA binds to a biotin-labelled oligo (dT)20 probe, which can then be immobilized by binding to streptavidin-coated magnetic particles. Magnetic separation kits are available for isolation of mRNA from total RNA, human or animal tissues or cells, and mammalian blood. In the mRNA isolation kit for white blood cells, an intermediate step is included to isolate total RNA. Total nucleic acids bind to the silica surface of magnetic glass particles. The glass particles are separated magnetically, and the nucleic acids eluted. The mRNA is then isolated using biotin-labelled oligo (dT) as in the other mRNA isolation kits.

This biotin-streptavidin binding strategy is also employed in ROCHE®'s mRNA capture kit, although this does not rely on magnetic separation. The kit is designed to immobilize mRNA in streptavidin-coated tubes for direct use in RT-PCR, making RNA isolation and the RT-PCR reactions a one-tube application. This is a valuable tool when using low-abundance mRNA or small amounts of starting material. The mRNA from lysed cells or tissues or from total RNA binds to biotin-labelled oligo (dT)20. Binding of the oligo (dT) to streptavidin-coated tubes serves to immobilize the mRNA, and the oligo (dT) serves as a functional primer for the reverse transcription reaction.

SERA-MAG® Magnetic oligo (dT), available from Alexon SERADYN® Inc., is made from 1 µm-diameter, carboxylate-modified, magnetic particles. The particles have a rough texture, offering a larger surface area for hybridization than would a smooth surface. Because of the very high surface concentration of oligo (dT)14 on these particles, SERADYN® claims that SERA-MAG® offers the highest poly(A)+ binding capacity available—1 ml of SERA-MAG® can bind up to 12 µg of mRNA from cells or tissue. Complete isolation kits are not yet available from SERADYN®, but sample sizes (1 ml) of SERA-MAG® Magnetic oligo (dT) are available in addition to larger volumes.

The mRNA Isolation Kit from Vector Laboratories Inc. is based on mRNA binding to magnetic oligo (dT)30 particles. The kit includes the magnetic separator rack required for magnetic separation. Paramagnetic streptavidin particles and biotin-oligo (dT)30 for indirect mRNA isolation are also available from Vector Labs.

Reference to "affinity chromatography" should be understood as a reference to any technique which separates the polyadenylated mRNA based on the affinity to the poly(A) tail for oligo(dT). For example, it encompasses all of the methods hereinbefore described.

In another embodiment, said affinity chromatography is oligo(dT) column chromatography.

As detailed hereinbefore, the method of the present invention has now made available membranous microvesicle populations, such as exosomes, at a level of purity not previously attainable. Accordingly, this has significant implications in terms of the application and use of membranous microvesicle populations such as exosomes. The therapeutic and diagnostic applications for exosomes, in particular, have been long recognised but have been held back due to difficulty in reliably and reproducibly isolating exosomes from biological samples. The method of the first aspect of the present invention therefore provides a simple, routine, yet improved outcome in terms of isolating the exosome populations themselves. These can be used therapeutically in their intact form or, as may be required for therapy—but in particular for diagnostics—they may be lysed and their proteinaceous, nucleic acid or other cytoplasmic components harvested and utilised.

To the extent that diagnostic applications are envisioned, the amplification, probing and/or other form of analysis of DNA and RNA will occur. Methods for isolating a total nucleic acid population, DNA alone and RNA alone are well known in the art and can be applied to the enriched membranous microvesicle population to obtain the desired nucleic acid population. As detailed in the context of the second aspect of the present invention, it has now been determined that exosomal mRNA is polyadenylated, this having now enabled the development of a routine means of specifically isolating the mRNA subpopulation.

As would be appreciated by the person of skill in the art, there are a wide variety of methods for amplifying DNA or RNA, these including, but not limited to:
(i) high multiplexity PCR based on PCR suppression;
(ii) on-chip PCR: DNA amplification and analysis on oligonucleotide microarrays;
(iii) long-distance single molecule PCR;
(iv) digital PCR analysis;
(v) real-time quantitative PCR ("real-time qPCR");
(vi) quantitative genetic analysis with multiplex ligation-dependent probe amplification (MLPA);
(vii) homogeneous real-time strand displacement amplification;
(viii) loop-mediated isothermal amplification (LAMP) of DNA analytes;
(ix) ligation-mediated rolling circle DNA amplification;
(x) rolling-circle amplification of duplex DNA sequences assisted by PNA openers;
(xi) Phi29 DNA polymerase based rolling circle amplification of templates for DNA sequencing;
(xii) multiple-displacement amplification (MDA);
(xiii) polymerase chain reaction;
(xiv) NASBA;
(xv) ligase chain reaction;
(xvi) strand displacement amplification
(xvii) T7 linear amplification;
(xviii) SMART amplification;
(xix) global PCR amplification;
(xx) Real Time PCR;
(xxi) reverse-transcriptase PCR (RT-PCR).

Reference to RT-PCR should be understood to encompass all forms of RT-PCR including, for example, 1-step RT-PCR, 2-step RT-PCR, quantitative RT-PCR, real time RT-PCR and quantitative real time RT-PCR.

However, although any of these well known methods could be applied to analyse membranous microvesicle nucleic acid molecules, in a third aspect of the present invention, and in terms of analysing specific mRNA transcripts, two protocols have been developed which unexpectedly achieve better amplification outcomes than alternative protocols which could be used.

Accordingly, in yet another aspect of the present invention there is provided a method of obtaining amplified membranous microvesicle RNA from a biological sample, said method comprising the steps of:
(i) subjecting said biological sample to mechanical cellular rupture wherein said mechanical cellular rupture selectively ruptures cells but not exosomes;
(ii) contacting the sample of step (i) with an RNA degradation enzyme for a time and under conditions sufficient to degrade free RNA;
(iii) lysing the exosomes obtained in accordance with step (ii);
(iv) isolating the polyadenylated RNA using oligo(dT) affinity chromatography; and
(v) amplifying the RNA of step (iv).

In one embodiment, said amplification is performed using RT-PCR, for example 1-step or 2-step RT-PCR.

In another embodiment, said mechanical cellular rupture is effected via centrifugation.

In still another embodiment, said centrifugation is performed at 15,000 g-17,000 g, preferably at 2° C.-9° C., most preferably at 4° C.

In a further embodiment, said centrifugation is performed at about 16,000 g, preferably for about 10 minutes.

In still another embodiment, said mechanical cell rupture is effected via bead milling.

In one embodiment, said bead is 0.1-0.5 mm in diameter.

In another embodiment, said sample is bead milled at approximately 20-40 Hz, preferably about 30 Hz, for 2-5 minutes.

In yet another embodiment, said beads are glass beads.

In yet another embodiment, said membranous microvesicle is an exosome.

In still another embodiment, said biological sample is blood, serum, plasma, saliva, urine or stool.

In one embodiment there is therefore provided a method of obtaining amplified exosomal RNA of interest from a biological sample, said method comprising the steps of:
(i) subjecting the biological sample to centrifugation at 15,000 g-17,000 g;
(ii) contacting the sample of step (i) with an RNA degradation enzyme for a time and under conditions sufficient to degrade free RNA;
(iii) lysing the exosomes obtained in accordance with step (ii);
(iv) isolating the polyadenylated RNA using oligo(dT) affinity chromatography; and
(v) amplifying the RNA step of (vi) using a 1-step or 2-step RT-PCR.

In another embodiment there is provided a method of obtaining amplified exosomal RNA of interest from a biological sample, said method comprising the steps of:
(i) subjecting the biological sample to bead milling;
(ii) contacting the sample of step (i) with an RNA degradation enzyme for a time and under conditions sufficient to degrade free RNA;
(iii) isolating the polyadenylated RNA using oligo(dT) affinity chromatography; and
(iv) amplifying the RNA step of (iii) using a 1-step or 2-step RT-PCR.

In one embodiment said RNA has been eluted in about 35 µl of RNase free water, using a 1-step RT-PCR protocol in a reaction volume of about 50 µl.

In yet another embodiment, said PCR is 1-step RT-PCR according to the GENEAMP® EZ rTth RNA RT-PCR protocol.

In yet another embodiment, said biological sample is subjected to an initial crude enrichment for the exosomes in a biological sample, such as preliminary centrifugation.

In another embodiment, said biological sample is a human biological sample.

In yet another embodiment, the initial crude centrifugation steps are performed at about 1,500 g for about 10 minutes and at about 4° C.

Without limiting the present invention to any one theory or mode of action, 1-step RT-PCR is a single-tube reaction which either uses a mixture of a reverse transcriptase and a traditional thermostable DNA polymerase or uses a thermostable DNA polymerase, such as that from *Thermus thermophilus* (Tth), which exhibits reverse transcriptase activity in addition to DNA polymerase activity in the presence of $Mn^{2+}$ ions. 2-step RT-PCR consists of two separate reactions. In the first reaction, an RNA strand is reverse transcribed into its complementary DNA (cDNA) using the enzyme reverse transcriptase. A portion of the first reaction, containing the produced cDNA, is then added to a second reaction containing a thermostable DNA polymerase, which through traditional PCR, amplifies the cDNA many fold.

Examples of commercially available 1-step and 2-step RT-PCR kits include, but are not limited to:

(i) 1-Step Kits.

ROCHE® LIGHTCYCLER® 480 RNA Master Hydrolysis Probes: A hot start reaction mix, specifically adapted for one-step RT-PCR. The kit provides reagents, including an RNA master mix (with buffer, nucleotides, and enzyme), a $Mn(OAc)_2$ stock solution, PCR-grade water, and enhancer solution.

QIAGEN® OneStep RT-PCR Kit: The QIAGEN® One-Step RT-PCR Kit provides a blend of Sensiscript and Omni script Reverse Transcriptases, HOTSTARTAQ® DNA Polymerase, QIAGEN® OneStep RT-PCR Buffer, a dNTP mix, and Q-Solution, a novel additive that enables efficient amplification of "difficult" (e.g., GC-rich) templates.

APPLIED BIOSYSTEMS® TAQMAN® RNA-TO-CT™ 1-Step Kit: Includes: 40×RT enzyme mix containing ARRAYSCRIPT™ UP Reverse Transcriptase, RNase Inhibitor; 2× master mix containing AMPLI-TAQ GOLD® DNA Polymerase UP, dNTPs (including dUTP), Passive Reference 1, and optimized buffer components.

AFFYMETRIX®/USB® One-Step RT-PCR Kit: The USB One-Step RT-PCR Kit uses M-MLV Reverse Transcriptase and Taq DNA Polymerase, premixed together at concentrations optimized to balance sensitivity and specificity. It also includes an optimized reaction buffer, RNase Inhibitor, Ultrapure dNTPs, supplemental magnesium chloride, and RNase-free water.

(ii) 2-Step Kits

QIAGEN® LongRange 2Step RT-PCR Kit: Reverse transcription step—LongRange Reverse Transcription Enzyme, Buffer, dNTPs, Oligo-dT, RNase Inhibitor, RNase-Free Water; PCR step—QIAGEN® LongRange PCR Kit (LongRange PCR Enzyme Mix, LongRange PCR Buffer, 5× Q-Solution, RNase-Free Water, 10 mM dNTPs).

APPLIED BIOSYSTEMS® TAQMAN® RNA-TO-CT™ 2-Step Kit: The TAQMAN® RNA-TO-CT™ 2-Step Kit is a combination of the High Capacity RNA-to-cDNA Kit and the TAQMAN® Gene Expression Master Mix. The High Capacity RNA-to-cDNA Kit is used to first reverse transcribe RNA into cDNA and the resulting cDNA is then quantified using the TAQMAN® Gene Expression Master Mix for real-time PCR.

AFFYMETRIX®/USB® Two-Step RT-PCR Kit: The USB Two-Step RT-PCR Kit uses M-MLV Reverse Transcriptase and Taq DNA Polymerase, provided in individual tubes at concentrations optimized to balance sensitivity and specificity in two-step RT-PCR. Optimized RT and PCR reaction buffers, RNase Inhibitor, Ultrapure dNTPs, supplemental magnesium chloride and RNase-free water are also included. A simple enzyme dilution step also allows use of the kit for one-step RT-PCR.

Reference to "using" the protocols of the commercial kits referenced herein should be understood as a reference to the use of the methods and reagents as specified in these kits, and as detailed herein in the examples, but is not limited to the use of these particular commercial kits themselves. That is, based on the information provided herein, the methods described in these kits could be performed using reagents and equipment which have been otherwise sourced and assembled. It should also be understood that the claims of this aspect of the invention, to the extent that they make use of the protocols in these kits, are not intended to be limited to the protocols as literally recited in the kits but include variations to the protocols which the skilled person would understand could be introduced without substantially changing the output which is obtainable. To this end, the kits recited in these claims are the subject of patents and patent applications in relation to the protocols and reagents, these documents typically describing the breadth of the variations which can be introduced to these methods without substantially impacting on the effectiveness of the method. For example, the QIAAMP® silica gel membrane technology is encompassed by, inter alia, U.S. Pat. No. 5,234,809, European Patent No. 0,389,063 and equivalents in other jurisdictions. The GENEAMP® rTth RNA PCR kit falls within the scope of U.S. Pat. Nos. 5,035,996; 5,638,896; 5,945,313; 6,287,823; 6,518,026; 4,683,202; 4,683,195; 4,965,188; 5,407,800; 5,322,770; 5,310,652 and their non-US counterparts. The contents of these specifications should be understood to be incorporated herein.

Reference to the term "about" in the context of these aspects of the present invention should be understood to have the same meaning as hereinbefore defined.

In yet another aspect of the present invention, there is provided a method of obtaining amplified membranous microvesicle mRNA from a biological sample, said method comprising the steps of:

(i) subjecting said biological sample to mechanical cellular rupture wherein said mechanical cellular rupture selectively ruptures cells but not exosomes;

(ii) contacting the sample of step (i) with an RNA degradation enzyme for a time and under conditions sufficient to degrade free RNA;

(iii) isolating the RNA using the QIAAMP® circulating nucleic acid kit protocol but wherein:
 (a) the ACW2 butter wash step of the QIAAMP® silica column is performed twice;
 (b) the ethanol wash step of the QIAAMP® silica column is performed twice;
 (c) the RNA is eluted in a final volume of about 35 µl;
 (d) the eluate of step (c) and AVE buffer are reapplied to the column; and (iv) amplifying the RNA of step (iii).

In one embodiment, said mechanical cellular rupture is effected via centrifugation or bead milling.

In still another embodiment, said centrifugation is performed at 15,000 g-17,000 g, preferably at 2° C.-9° C., most preferably at 4° C.

In a further embodiment, said centrifugation is performed at about 16,000 g, preferably for about 10 minutes.

In still another embodiment, said mechanical cell rupture is effected via bead milling.

In one embodiment, said bead is 0.1-0.5 mm in diameter.

In another embodiment, said sample is bead milled at approximately 20-40 Hz, preferably about 30 Hz, for 2-5 minutes.

In yet another embodiment, said beads are glass beads.

In a further embodiment, said PCR is 1-step or 2-step RT-PCR.

In yet another embodiment, said membranous microvesicle is an exosome.

In still another embodiment, said biological sample is blood, serum, plasma, urine, stool, ascites, cerebrospinal fluid or saliva.

In a further embodiment the present invention provides a method of obtaining amplified exosome mRNA from a biological sample, said method comprising the steps of:

(i) subjecting the biological sample to either centrifugation at 15,000 g-17,000 g or bead milling;
(ii) contacting the sample of step (i) with an RNA degradation enzyme for a time and under conditions sufficient to degrade free RNA;
(iii) isolating the RNA using the QIAAMP® circulating nucleic acid kit protocol but wherein:
(a) the ACW2 butter wash step of the QIAAMP® silica column is performed twice;
(b) the ethanol wash step of the QIAAMP® silica column is performed twice;
(c) the RNA is eluted in a final volume of about 35 µl;
(d) the eluate of step (c) and AVE buffer are reapplied to the column; and
(iv) amplifying the RNA of step (iii) by RT-PCR.

In one embodiment said PCR is 1-step or 2-step RT-PCR.

In another embodiment, said 1-step PCR is performed using the GENEAMP® EZ rTth RNA PCR protocol.

In yet another embodiment, the PCR is performed in a reaction volume of about 50 µl.

In yet still another embodiment, said biological sample is a human biological sample.

In still another embodiment, the biological sample is subjected to an initial crude enrichment for the exosomes in a biological sample, such as by preliminary centrifugation.

In yet still another embodiment, the initial centrifugation of steps are performed at about 1,500 g for about 10 minutes and at about 4° C. and the centrifugation is performed at about 16,000 g for about 10 minutes and at about 4° C.

In still another embodiment, said mechanical cell rupture is effected via bead milling.

In one embodiment, said bead is 0.1-0.5 mm in diameter.

In another embodiment, said sample is bead milled at approximately 20-40 Hz, preferably about 30 Hz, for 2-5 minutes.

In yet another embodiment, said beads are glass beads.

In this regard, it should be understood that the present invention may optionally comprise one or more additional steps. The person of skill in the art may elect to introduce additional steps which may be particularly useful with respect to a given situation. For example, and as detailed hereinbefore, the means of isolating and preparing a biological sample for use in accordance with the method of the present invention will likely vary according to the nature of the sample itself. Suitable preparative protocols could be routinely determined by the person of skill in the art based on common knowledge and experience. In another example, in certain circumstances the person of skill in the art may elect to introduce a purification step such as a cesium chloride separation step in order to separate double versus single stranded nucleic acid molecules. Such techniques may be particularly suitable for separating single stranded RNA from double stranded DNA. The applicability of such a step would likely depend on the outcome to be achieved and on the nature of the biological sample from which the nucleic acid molecules are being isolated. In yet another example, although the preferred method is to isolate RNA, to the extent that it may be necessary to rupture cellular nuclei which are present in a biological sample, thereby facilitating access to genomic DNA.

The amplification steps of the present invention rely on the use of primers. Reference to a "primer" or an "oligonucleotide primer" should be understood as a reference to any molecule comprising a sequence of nucleotides, or functional, derivatives or analogues thereof, the function of which includes hybridisation to a region of a nucleic acid molecule of interest. It should be understood that the primer may comprise non-nucleic acid components. For example, the primer may also comprise a non-nucleic acid tag such as a fluorescent or enzymatic tag or some other non-nucleic acid component which facilitates the use of the molecule as a probe or which otherwise facilitates its detection or immobilisation. The primer may also comprise additional nucleic acid components, such as the oligonucleotide tag which is discussed in more detail hereinafter. In another example, the primer may be a protein nucleic acid which comprises a peptide backbone exhibiting nucleic acid side chains. Preferably, said oligonucleotide primer is a DNA primer.

The design and synthesis of primers suitable for use in the present invention would be well known to those of skill in the art. In one embodiment, the subject primer is 4 to 60 nucleotides in length, in another embodiment 10 to 50 in length, in yet another embodiment 15 to 45 in length, in still another embodiment 20 to 40 in length, in yet another embodiment 25 to 35 in length. In yet still another embodiment, primer is about 26, 27, 28, 29, 30, 31, 32, 33 or 34 nucleotides in length.

Various techniques can be used to analyse an amplification product. Their operational characteristics, such as ease of use or sensitivity, vary so that different techniques may be useful for different purposes. They include but are not limited to:
Sequencing
Pyrosequencing
Enzyme digestion
Microarray analysis
Denaturing gradient gel electrophoresis
Agarose gel based separation
Melt curve analysis on real-time PCR cyclers
Quantitative real-time PCR
Denaturing high performance liquid chromatography
Mass spectrometry
Primer extension
Oligonucleotide-ligation
Mutation specific polymerase chain reaction
Denaturing gradient electrophoresis (DGGE)
Temperature gradient denaturing electrophoresis
Constant denaturing electrophoresis
Single strand conformational electrophoresis
Denaturing high performance liquid chromatography (DHPLC)

In a further aspect there is provided a kit for enriching for membranous microvesicles in a biological sample, said kit comprising instructions and optionally reagents to effect mechanical cellular rupture wherein said mechanical cellular rupture selectively ruptures cells but not membranous microvesicles. The kit optionally comprises a facility for storing said biological sample.

In one embodiment, said kit further provides instructions and reagents to effect RNA isolation and/or application as hereinbefore described in detail.

The present invention is further described by reference to the following non-limiting examples.

Example 1

Disruption of Blood Cells

Membranous microvesicles are currently isolated either by 1) immunocapture (using antibodies targeting surface exposed proteins on membranous microvesicles) or by 2) several ultracentrifugation steps. Both of these methods are laborious and require special instrumentation.

Figure 3:
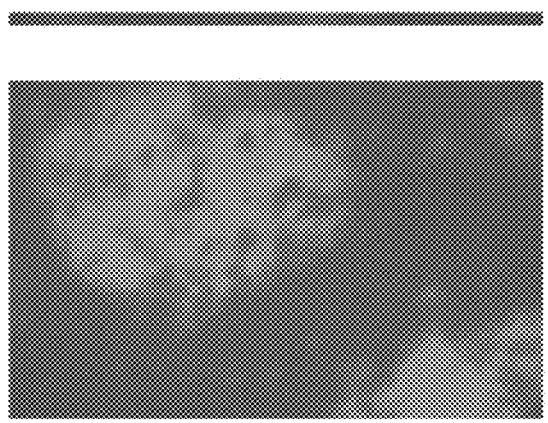
FIG. 3. DAPI-staining based examination of the 16,000 generated pellet. Fluorescent microscopy image of an aliquot of the pellet, generated after the third 16,000 g, resuspended in a 4',6-diamidono-2-phenylindole (DAPI) solution (Invitrogen). No intact cell nuclei were detectable.

A. Using a conventional blood sampling protocol (two consecutive centrifugation steps of 1,500 g, 10 minutes, 4° C.), GAPDH mRNA has been detected in RNA isolated from the resulting plasma from more than +100 donor patients, +100 patients with colorectal adenomas and +100 patients with colorectal cancer (CRC).
B. Despite current dogma that two consecutive centrifugation steps are enough to pellet cells of haematopoietic origin, it has been shown that the introduction a third centrifugation step of 16,000 g (10 minutes, 4° C.) resulted in:
  1. RNA signal loss>95% which was not recoverable in the pellet generated after the 16,000 spin (FIG. 1 and Table 1: Sample 1 and Sample 3 relative to Sample 1).
  2. A DAPI-staining of the 16,000 g-derived pelleted material showed no evidence of intact nuclei (FIG. 3) and hence exposure of the cellular RNA content to the ribonucleases in plasma.
  3. Released cellular RNA as an effect of a 16,000 g centrifugation spin can be preserved if an RNA preservative such as that found in PAXGENE® RNA blood tubes (FIG. 1 and Table 1: Sample 4 versus Sample 1) is added prior to the 16,000 g spin.

Thus, a 16,000 g centrifugation step efficiently disrupts cells and removes intracellular content of RNA due to exposure to circulating RNAses in blood.

The measured GAPDH RNA signal (Example 8) in this cell-free plasma is protected from plasma ribonucleases, i.e. derived from membranous microvesicles/microparticles. The demonstrated rupture of the 16,000 g pelleted blood cells implies that subsequent isolation of the resulting plasma liquid is not necessary prior to extracting the RNA for GAPDH RT-PCR analysis.

Example 2

Methods 40 mL of plasma was prepared from whole blood by two centrifugations at 1500×g/10 min/4° C. and pooled. Armored RNA (20 uL; 2.5 uL per 5 mL) was added and mixed. 5 mL was retained as 1500×g plasma (sample #1). 8 tubes with 1 mL each were milled with 1.0 g 0.1 mm beads (sample #2). 8 tubes with 1 mL each were milled with 1.0 g 0.5 mm beads (sample #3). The remaining 19 mL plasma was centrifuged at 16,000×g/10 min/4° C., from which 3×5 mL aliquots were collected. One 5 ml aliquot was used as Sample #4 below.

| Number | Bead weight | Bead diameter | milling time (min) | Plasma added |
| --- | --- | --- | --- | --- |
| 1 (1500xg non-milled control) | nil | nil | nil | 5 mL |
| 2 | 0.5 g | 0.1 mm | 4 | 1 mL (x8 tubes) |
| 3 | 1.0 g | 0.1 mm | 4 | 1 mL (x8 tubes) |
| 4 (16000xg control) | NA | NA | nil | 5 mL |

For each bead-milled set of 8 tubes (samples 2 and 3), the tubes were fitted into the 24-tube racks of the Tissuelyser, and shaken at 30 Hz for 2 min/room temp, unassembled, the inner plastic rack rotated 180°, reassembled and re-shaken at 30 Hz for 2 min/room temp. Following bead milling, tubes were returned to ice, and spun at 1500×g/5 min/4° C. 653 uL supernatant was collected per tube and pooled into a 50 mL tube.

Samples were processed by the standard QIAAMP® kit with the following modifications: (i) The 9 mL ACB binding buffer was supplemented with 5.6 mL Isopropanol and (ii) elution was done with columns at 70° C. using AVE pre-warmed at 70° C. (2 successive elutions using the one 35 μL AVE aliquot).

One-step Tth qRT-PCR was performed using the ROCHE® LIGHTCYCLER® 480 RNA Master Hydrolysis Probes Kit (including Uracil DNA Glycosylase), using 2 uL template per assay. PCR targets were GAPDH 5', Armored RNA, CD45, FasLigand and TRAIL (TNSF10). A GAPDH 5' standard curve was also run.

Figure 6:
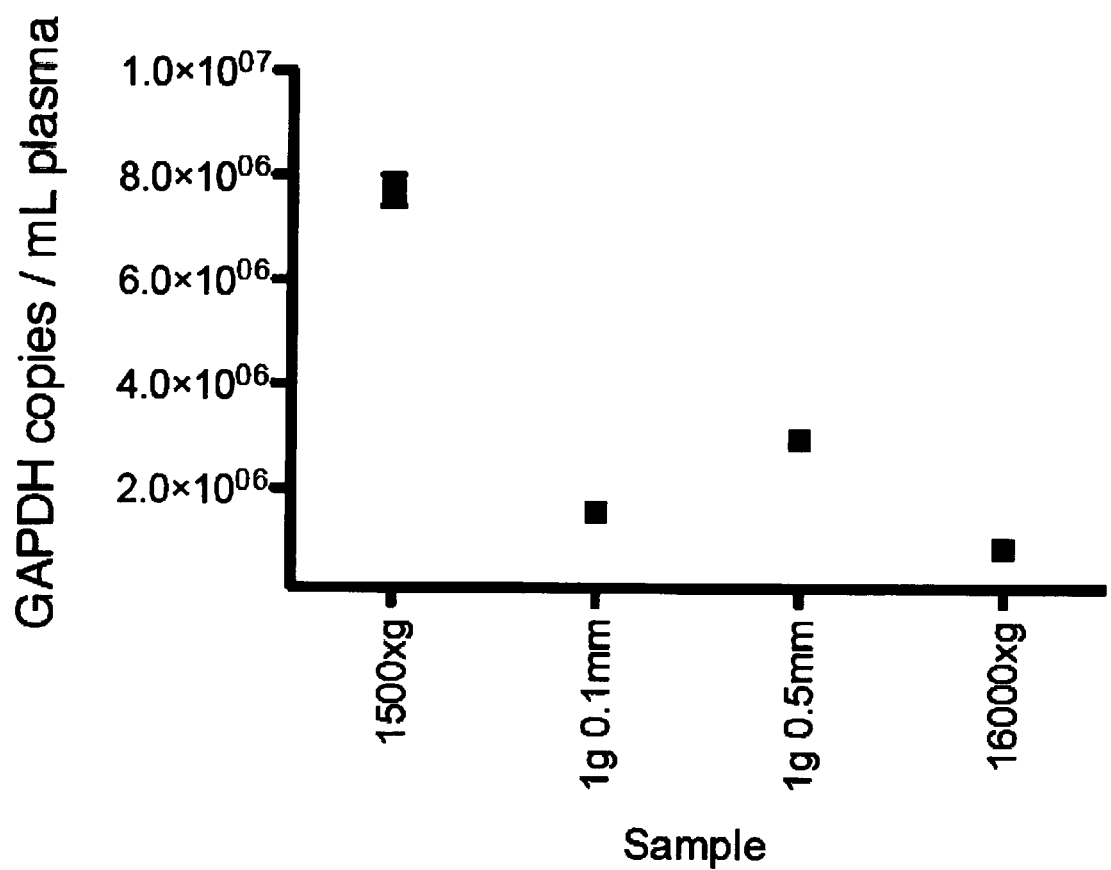
FIG. 6: GAPDH copy number before and after bead milling of plasma. Samples are indicated under the X axis, and are all 1500×g plasma except the far right sample.

With all targets (except Armored RNA), the bead milled samples are intermediate between the non-milled 1500×g and 16000×g samples, confirming that the bead milling process had worked (in that it increased C(t) towards that of 16000×g plasma). The bead milling that gave the greatest reduction in yield was 1.0 g of 0.1 mm beads per mL of plasma The GAPDH samples were quantified from the standard curve. The 1500×g plasma contains 7.7×10e6 copies per mL of plasma. The 16000×g sample contains 9.485×10e5 copies per mL, which is 12.3% of the 1500×g plasma (a loss of 88%). The 1.0 g of 0.1 mm beads milled sample contains 1.575×10e6 copies per mL, which is 20.45% of the 1500×g sample (a loss of 80%). The 1.0 g of 0.5 mm beads milled sample contains 2.943×10e6 copies per mL, which is 38.22% of the 1500×g sample (a loss of 62%). This data is shown in FIG. 6.

The CD45, TRAIL and Fas Ligand data cannot be similarly quantified because standard curves could not be run (no RNA standards available). However, on the assumption that 1 C(t) unit represents a 2-fold change in copy number, then:
  CD45: 0.5 mm beads=34% loss; 0.1 mm beads=56% loss; 16000×g=81% loss
  TRAIL: 0.5 mm beads=12% loss; 0.1 mm beads=61% loss; 16000×g=81% loss
  FasL: 0.5 mm beads=60% loss; 0.1 mm beads=72% loss; 16000×g=87.5% loss
  GAPDH*: 0.5 mm beads=57% loss; 0.1 mm beads=75% loss; 16000×g=84% loss Here, GAPDH is calculated assuming 1 C(t)=2-fold change; results differ slightly from the standard curve above.

Figure 5:
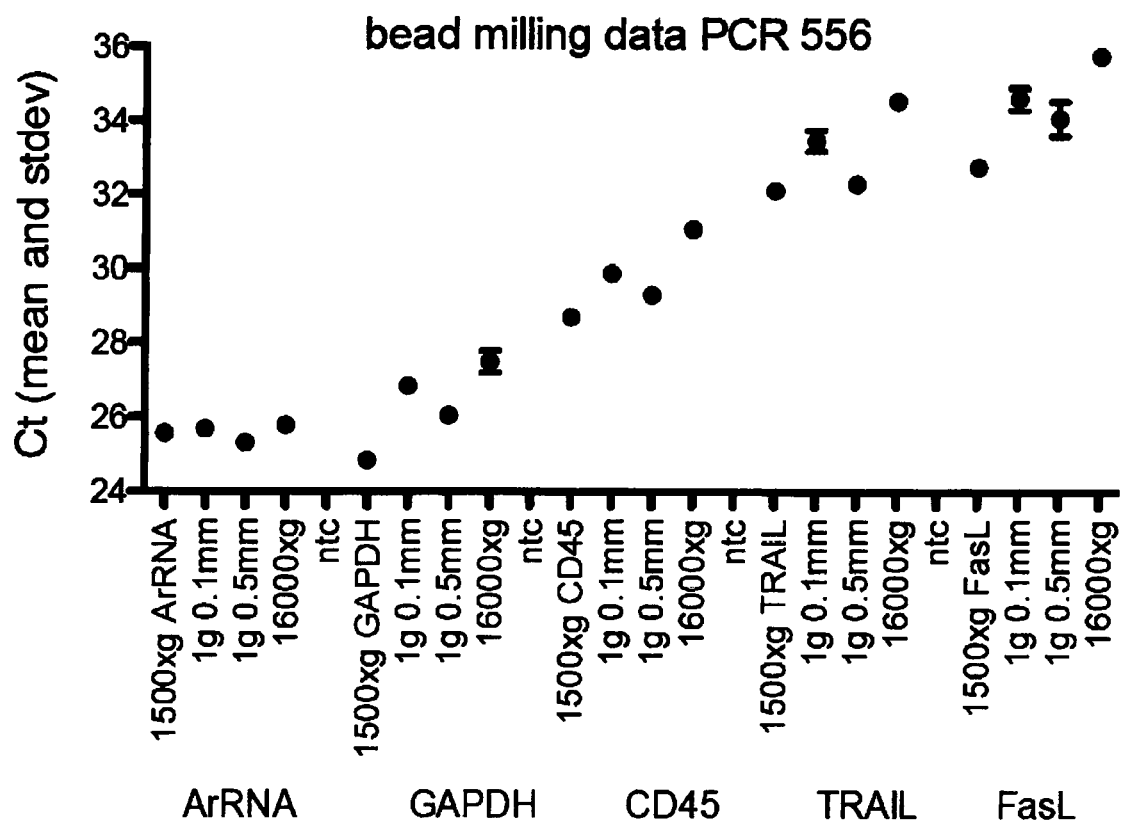
FIG. 5: Effect of bead milling on spiked armored RNA and other targets Samples are indicated under the X axis, with the PCR target indicated below each group. Data points are mean+/−SD of duplicate measurements.

The armored RNA (2.5 uL) was added to each 5 mL plasma sample before the bead milling process and sample lysis. Therefore, it can be used to assay the effect of bead milling. All samples exhibit an ArRNA C(t) in the narrow range of 25.33 to 25.79 and all look similar on the left of FIG. 5. The ArRNA data has been enlarged on the right of FIG. 5. The 1500×g sample has a C(t) of 25.575. This does increase very slightly to 25.69 after milling with 0.1 mm beads, which could indicate some lysis of ArRNA-bacteriophage particles, but milling with 0.5 mm beads actually gives an earlier C(t) of 25.33, suggesting a gain in RNA yield. Given that milling with 0.5 mm beads also generally increases C(t) values (i.e., later C(t)), these changes in ArRNA C(t) values presumably reflect losses incurred during sample preparation, rather than losses due to the beads disrupting the ArRNA pseudo-bacteriophage. With the 16000×g control sample, the ArRNA C(t) increased slightly to 25.79, compared to 25.575 for the 1500×g plasma. This could be consistent with some loss of pseudo-bacteriophage at the higher g-forces, but is more likely variation in sample preparation.

For comparison, the change in ArRNA signal was calculated as above, assuming 1 C(t)=2-fold:

rRNA: 0.5 mm beads=18% gain; 0.1 mm beads=7.5% loss; 16000×g=14% loss

Clearly, ArRNA is not mirroring the systematic signal loss seen with other RNA targets, and thus it can be concluded that the armored RNA pseudo-bacteriophage particles are not affected by the bead milling process.

Conclusions.

1. The bead milling that gave the greatest reduction in yield was 1.0 g of 0.1 mm beads per mL of 1500×g plasma, milled for 2×2 min at 30 Hz.
2. The armored RNA (that was spiked in before bead milling and/or 16000×g centrifugation) gave approximately similar C(t) values for all conditions, within experimental error. Thus the bead milling protocol does not lyse the 26 nm diameter ArRNA pseudo-bacteriophage (assuming it has the same diameter as a true M2).

1. PCR cocktail: GAPDH5' in-house assay; 25 uL reaction volume

| component | per well | x24 well cocktail |
|---|---|---|
| LC480 Tth master hydrolysis probe (#1) | 9.25 | 222 |
| Fwd primer (GAA GGT GAA GGT CGG AGT (SEQ ID NO: 1), 10 uM) | 0.5 | 12 |
| Rev primer (GAA GAT GGT GAT GGG ATT TC (SEQ ID NO: 2), 10 uM) | 0.5 | 12 |
| probe ([6FAM] CAA GCT TCC CGT TCT CAG CC [TAM] (SEQ ID NO: 3), 10 uM) | 0.25 | 6 |
| activator (kit tube #2) | 1.625 | 39 |
| enhancer (kit tube #4) | 1.25 | 30 |
| nuclease-free water | 10.125 | 219 |
| RNA template | 1 | — |
| UNG | 0.5 | 12 |

2. PCR cocktail: commercial TAQMAN® (CD45; FasL; TRAIL[TNFSF10]); 25 uL reaction volume

| component | per well | x14 well cocktail |
|---|---|---|
| LC480 master hydrolysis probe | 9.25 | 129.5 |
| 20x TAQMAN ® | 1.25 | 17.5 |
| Activator | 1.625 | 22.75 |
| Enhancer | 1.25 | 17.5 |
| NFW | 9.125 | 128 |
| RNA | 2 | |
| UNG | 0.5 | 7 |

3. PCR cocktail: in-house Armored RNA; 25 uL reaction volume

| component | per well | x14 well cocktail |
|---|---|---|
| LC480 master hydrolysis probe | 9.25 | 129.5 |
| Fwd primer GAA TGC GGC TAA TCC CAA CCT CG (SEQ ID NO: 4), 50 uM | 0.2 | 2.8 |
| Rev primer GGA AAC ACG GAC ACC AAA AGT AG (SEQ ID NO: 5), 50 uM | 0.2 | 2.8 |
| Probe [6FAM] TGC GCG TTA CGA CAG GCC AAT CAC T [TAM] (SEQ ID NO: 6), 10 uM | 0.5 | 7 |
| activator | 1.625 | 22.75 |
| enhancer | 1.25 | 17.5 |
| NFW | 9.6 | 134.4 |
| RNA | 2 | |
| UNG | 0.5 | 7 |

4. PCR cocktail: in-house KIAA_116 (with reduced REV primer); 25 uL reaction volume

| Roche 1 step kit | 1x (50 ul reaction volume) | x21 cocktail = 42 @ 21.5 uL |
|---|---|---|
| LC480 RNA Master Hydrolysis Probe | 18.5 ul | 388.5 |
| activator | 3.25 ul | 68.25 |
| PCR grade water | 7.55 ul | 232 |
| enhancer | 2.5 ul | 52.5 |
| FWD primer GAA CTC GCC ATC TGG CTC A (SEQ ID NO: 7)-10 uM stock | 1 ul (final conc. 200 nM) | 21 |
| REV primer GGG TAG CAG AGC CCC ACT C (SEQ ID NO: 8)-10 uM stock | 1 ul (final conc. 200 nM) | 21 |
| probe [6FAM] ACT TCA ACA AGG GCG ACT GGA TCC [TAM] (SEQ ID NO: 9) -10 uM stock | 1.2 ul (final conc. 250 nM) | 25.2 |
| template | 3.5 ul | — |
| UNG | 1.0 | 21 |

5. PCR conditions:

| UNG treatment | 25° C. | 5 minutes |
|---|---|---|
| reverse transcription | 63° C. | 10 minutes |
| denaturation | 95° C. | 30 seconds |

| | | |
|---|---|---|
| Amplification (x60 cycles) | 95° C. | 15 seconds |
| | 60° C. | 60 seconds |
| | 72° C. | 1 second (acquisition) |
| Cooling | 40° C. | 10 seconds |

Example 3

Bead Milling as a Means for Isolation of Microvesicles

Materials:

Human plasma containing hepatitis-C virus (HCV plasma) was purchased from Acrometrix. HCV is a 50 nm diameter, lipid-membrane-enclosed particle, and is thus a mimic for exosomes (50-100 nm diameter lipid-membrane-enclosed vesicle). It has an RNA genome, which can be detected by qRT-PCR. This plasma was additionally spiked with (i) 100,000 human HCT116 cells (as a mimic for human cells present in plasma), that express a gene CDH3, which is not normally present in blood plasma, and whose mRNA can be detected by qRT-PCR; and (ii) armored RNA (ArRNA) particles, a ~30 nm diameter protein coat-enclosed particle containing a synthetic RNA, that can be detected by qRT-PCR.

Methods:

3 mL HCV plasma was spiked with 300,000 HCT116 cells plus 7.5 uL ArRNA.

1 mL of this plasma was set aside as Sample 1.

The remaining 2 mL was divided into 2×1 mL aliquots, 1 g of 0.1 mm glass beads was added, the samples bead-milled at 30 Hz for 4 min, spun briefly (5 sec 1000×g). 0.5 mL of supernatant was recovered from each tube and pooled to give Sample 2.

Figure 7:
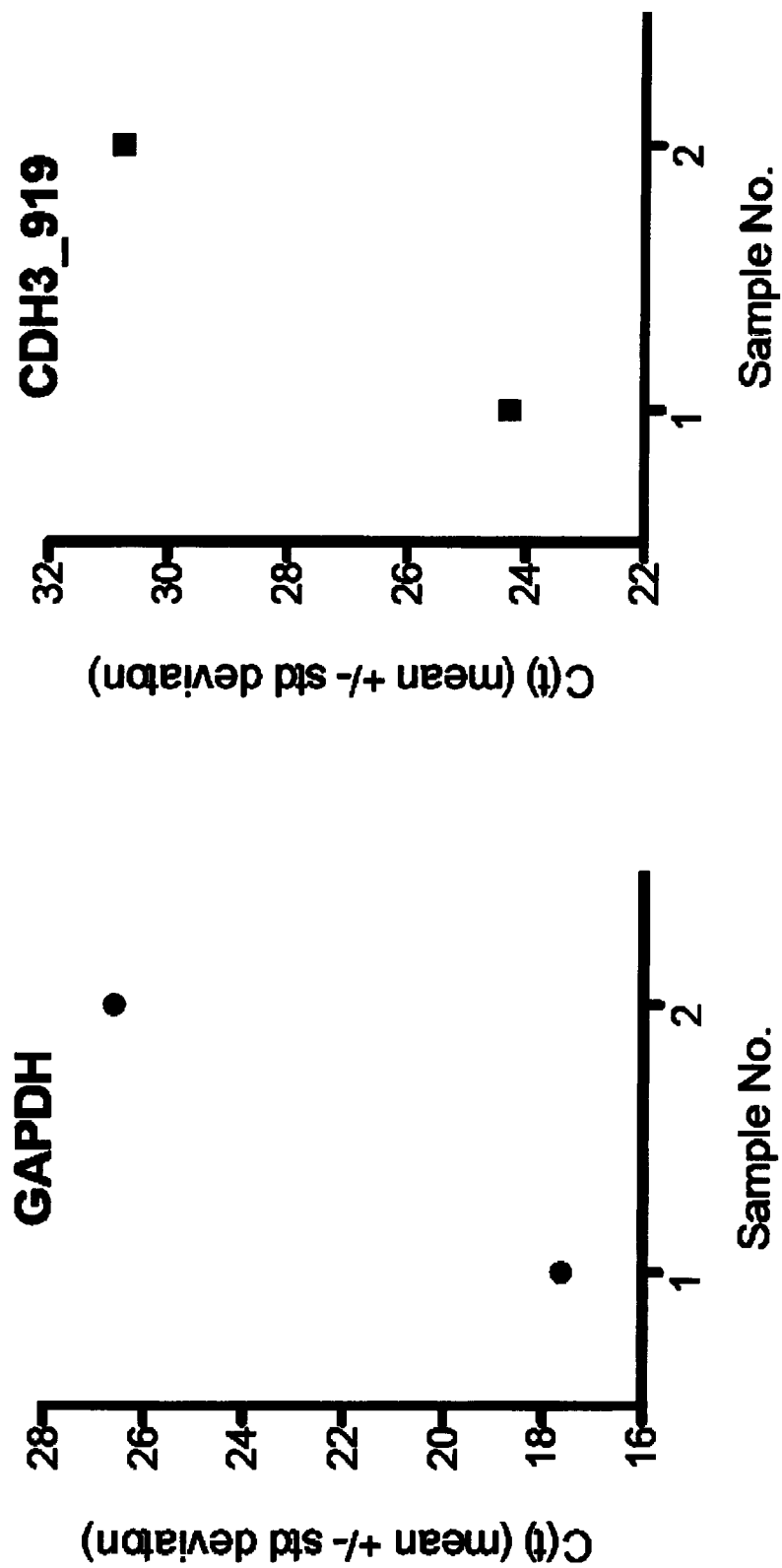
FIG. 7: Bead milling of plasma.
Figure 7:
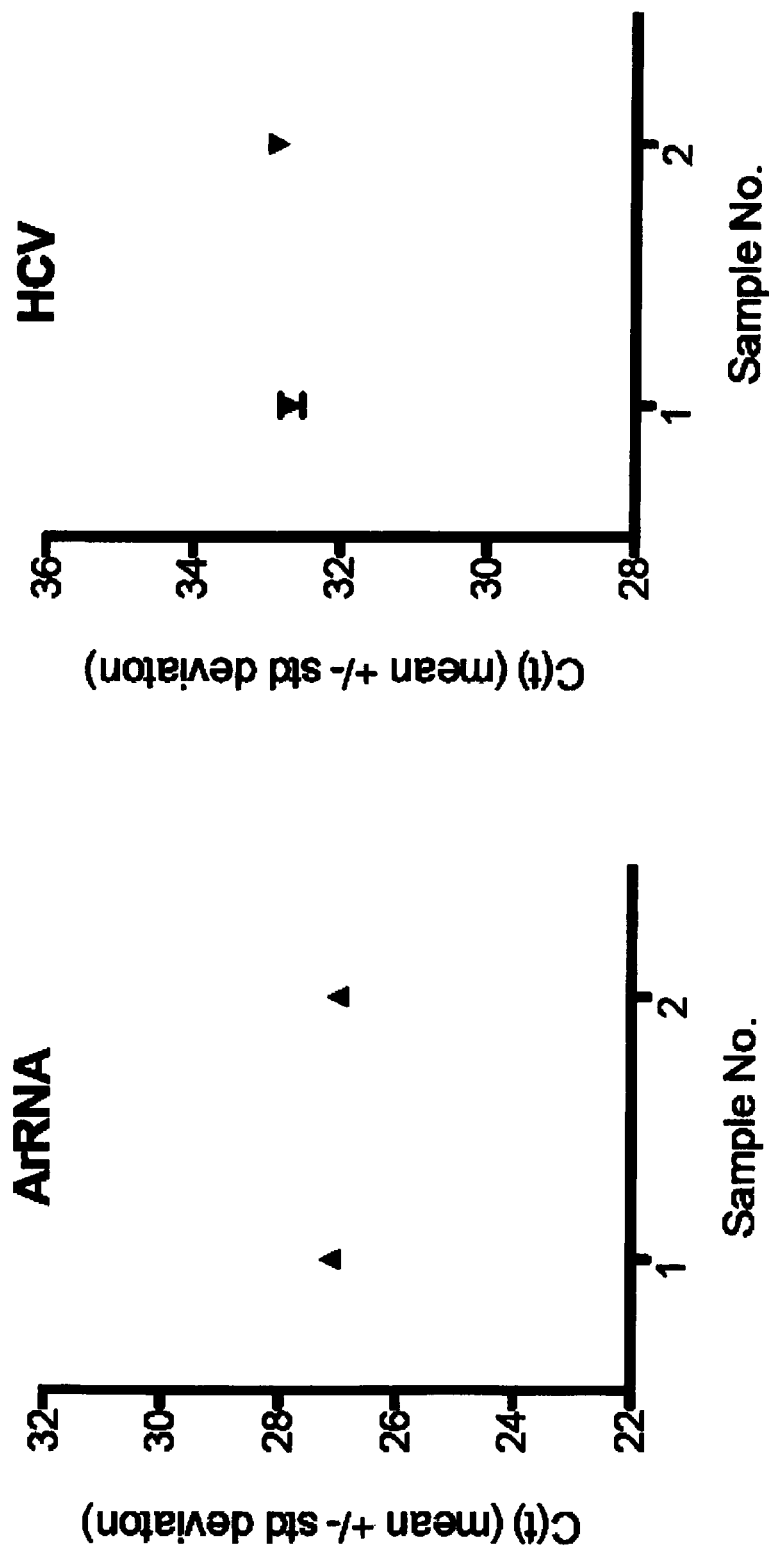

RNA was purified from both samples using the QIAAMP® circulating nucleic acids kit (QIAGEN®) and eluted with 35 uL volume. Duplicate 2 uL aliquots were assayed by qRT-PCR for the target indicated above each panel in FIG. 7.

Results:
1. GAPDH levels (top left panel) decrease dramatically after bead milling (99.8% loss)
2. CDH3 levels (top right panel) decrease dramatically after bead milling (99.56% loss)
3. ArRNA levels remain constant before and after bead milling (bottom left panel). Thus ArRNA (30 nM protein-coated RNA species) survives bead milling.
4. HCV levels remain constant before and after bead milling (bottom right panel). Thus HCV (50 nm lipid-coated/protein coated RNA genome) survives bead-milling intact.

Notes: HCT116 cells are spiked into plasma as a model of intact white-blood cells. Most of the GAPDH and CDH3_919 signal originates from the HCT116 cells rather than GAPDH and CDH3 RNA present in the plasma.

Conclusion:

Bead-milling results in almost complete removal of RNA signals from intact cells in plasma, while not affecting RNA enclosed by microvesicle-sized particles. Bead milling is thus an efficient method of removing RNA signals from contaminating intact cells in plasma and other fluids.

Example 4

Centrifugation as a Means for Isolation of Microvesicles

Materials:

Human plasma was prepared from whole human blood obtained from the Australian Red Cross by two successive centrifugations at 1500×g for 10 min/4° C. The plasma was spiked with (i) 100,000 human HCT116 cells (as a mimic for human cells present in plasma), that express a gene CDH3, which is not normally present in blood plasma, and Whose mRNA can be detected by qRT-PCR; and (ii) armored RNA (ArRNA) particles, a ~30 nm diameter protein-coat-enclosed particle containing a synthetic RNA, that can be detected by qRT-PCR.

Methods:

3 mL human plasma was spiked with 300,000 HCT116 cells plus 7.5 uL ArRNA.

1 mL of this plasma was set aside as Sample 1.

The remaining 2 mL was divided into 2×1 mL aliquots and centrifuged at 1500×g for 10 min/4° C. The entire supernatant of one tube was collected and set aside as Sample 2. The entire supernatant of the other tube was collected into a fresh tube and centrifuged at 16,000×g for 10 min/4° C. The entire supernatant was collected and set aside as Sample 3.

Figure 8:
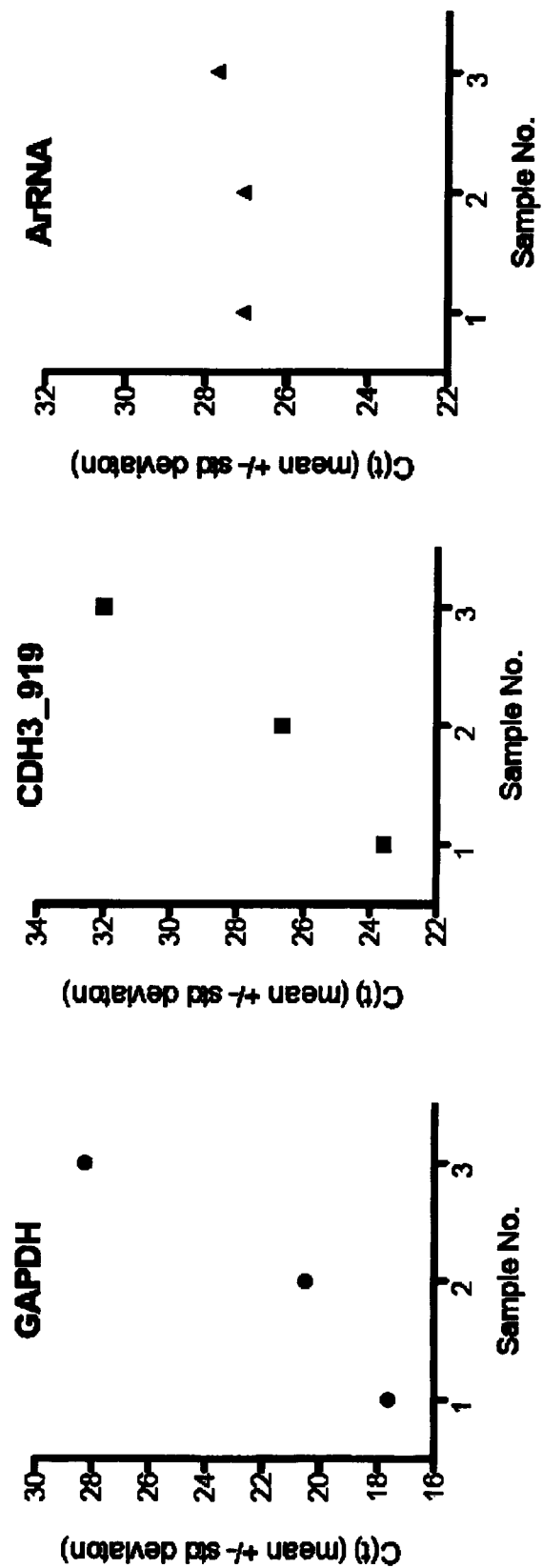
FIG. 8: Centrifugation of plasma.

RNA was purified from the three samples using the QIAAMP® circulating nucleic acids kit (QIAGEN®) and eluted with 35 uL volume. Duplicate 2 uL aliquots were assayed by qRT-PCR for the target indicated above each panel in FIG. 8.

Results:
(1) GAPDH levels (top left panel) decrease substantially after 1500×g centrifugation (86.7% loss) and more dramatically after 16000×g centrifugation (99.94% loss)
(2) CDH3 levels (top right panel) decrease substantially after 1500×g centrifugation (92% loss) and more dramatically after 16000×g centrifugation (99.91% loss)
(3) ArRNA levels remain constant across all samples (bottom left panel). Thus ArRNA (30 nM protein-coated RNA species) survives 16000×g centrifugation Notes: HCT116 cells are spiked into plasma as a model of intact white-blood cells. Most of the GAPDH and CDH3_919 signal originates from the HCT116 cells rather than GAPDH and CDH3 RNA present in the plasma.

Conclusion:

Centrifugation at 16000×g results in almost complete removal of RNA signals from intact cells in plasma, while not affecting RNA enclosed by microvesicle-sized particles. Centrifugation is thus an efficient method of removing RNA signals from contaminating intact cells in plasma and other fluids.

Example 5

Extraction of Total RNA from Circulating Microparticles

Figure 4:
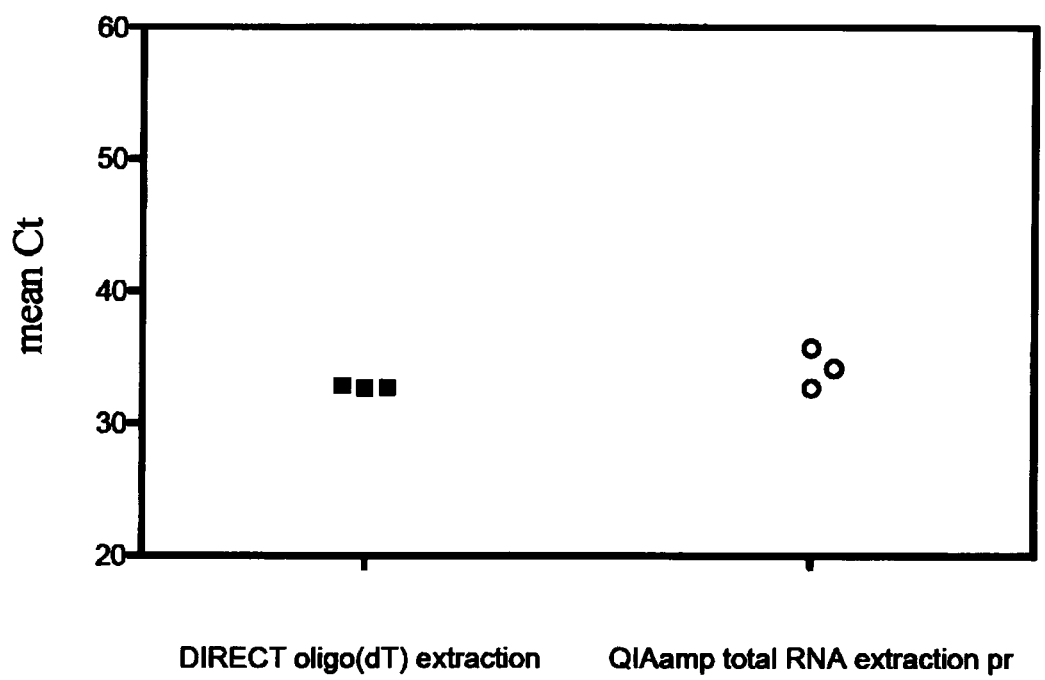
FIG. 4. Exosomal RNA contains poly(A) tails: 16,000 g centrifugation spins were applied to 2 ml plasma lots to disrupt residual haematopoietic cells. Total RNA or mRNA were subsequently extracted from the acellular plasma using the QIAamp circulating nucleic acid kit (circles) or the DIRECT oligo(dT) extraction kit (black squares). A GAPDH qPCR assay was used to measure the level of GAPDH RNA in the two extraction eluates.

1. Whole blood collected in EDTA tubes is centrifuged at 1500×g for 10 mins at 4° C. plasma is transferred into new tubes and centrifuged for second time at 1500×g. This plasma is then transferred to a fresh tube and centrifuged for a third time, this time at 16,000×g for 10 mins at 4° C. The resultant supernatant now constitutes an acellular solution containing intact microvesicles 2. 5 ml of acellular solution prepared using the 3 step centrifugation protocol described above was used for RNA extraction using the QIAAMP® circulating Nucleic acid Kit following manufacturers instructions, with exceptions being, column is washed twice with ACW2 and twice with ethanol (Example 7). The purified RNA was eluted in a final volume of 35 ul. The RNA can now be analysed as described in Example 8 (FIG. 4).

Example 6

1. Whole blood collected in EDTA tubes is centrifuged at 1500×g for 10 mins at 4° C., plasma is transferred into new tubes and centrifuged for a second time at 1500×g. This plasma is then transferred to a fresh tube and centrifuged for a third time, this time at 16,000×g for 10 mins at 4° C. The resultant supernatant now constitutes an acellular solution containing intact microvesicles
2. 2 ml of acellular solution prepared using the 3 step centrifugation protocol described above is used for extraction of polyadenylated mRNA using the DYNABEADS® mRNA DIRECT Kit (DYNAL® Biotech ASA, Oslo, Norway), Example 9.
3. Volume of lysis buffer was added per 1 volume of plasma and the mRNA eluted from the beads in 35 ul of RNase free water.
4. The mRNA can now be analysed as described in Example 8 (FIG. 4)

Example 7

QIAMP® Circulating Nucleic Acid Kit Protocol

Solid phase purification of nucleic acids by means of silica matrices is commonly used in commercially available kits. The principle of solid phase nucleic acid extractions is well described. The four key steps involved in solid-phase extraction are cell lysis, nucleic acids adsorption, washing, and elution. Cell lysis, inactivation of RNAses and denaturation of proteins can be obtained in one step by using chaotropic salts such as guanidine isothiocyanate based buffers with high pH. The cell lysis and protein denaturation can be further by proteinase K to the lysis buffer. Nucleic acids will adsorb to the column with the aid of high pH and high salt concentration. The adsorption process is based on the following principles: hydrogen-binding interaction with a hydrophilic matrix under chaotropic conditions, ionic exchange under aqueous conditions by means of an anion exchanger, and affinity and size exclusion mechanisms. Removal of the non-nucleic acid compounds, e.g. proteins, and the salt used to conditioning the column is obtained by several consecutive wash steps using buffers with increasing alcohol concentration. The bound nucleic acids are finally eluted using a Tris-EDTA buffer or water.

The QIAAMP® circulating nucleic acid kit protocol is based on solid-phase extraction of nucleic acids using a guanidine isothiocyanate buffer system ("QIAAMP® circulating Nucleic Acid Handbook, May 2009).

Materials
0.01M phosphate buffered saline [PBS] pH 7.4.
1500 KU DNAse I enzyme in 0.55 mL RNase free water.
Nuclease-free water. E.g. purchasable through PROMEGA® cat. no.: P1193.
20 mL columns which are adaptable to standard manifold
20 mL tube extenders
2 mL microfuge collection tubes
Carrier RNA (e.g. poly(A) RNA molecules>100 nt, sperm tRNA, etc). Stock concentration of 1 µg/µL RNA in nuclease-free water.
Proteinase K. Stock solution>600 mAU/mL
Lysis (Buffer ACL), binding (ACB), washing (ACW1 and ACW2) and elution buffer (AVE) are all provided in the QIAAMP® kit. The principle of these buffers are described in Gjerse et al. but they are contain:
  Buffer "ACL": 25-50% guanidine thiocyanate, 1-2.5% Tris+proteinase K
  Buffer "ACB": 25-50% guanidine thiocyanate, 1-2.5% Tris, 40% isopropanol
  Buffer "ACW1" 7 "ACW2": 50-100% Guanidium chloride, Ethanol
  Buffer "AVE": RNase-free water w/0.04% sodium-azice (v/v)

Protocol
1. Bring RNA-containing samples up to a final volume of 5 mL using 1×PBS
2. Add 500 uL Proteinase K, 4 mL Lysis buffer (e.g. ACL), 5.6 ug carrier RNA and incubate at 60° C. for 30 min.
3. Add 9 mL Binding buffer (e.g. ACB) and mix 30 sec. Incubate on ice for 5 min.
4. Apply the lysate to a silica-containing columns equipped with a tube extender of the QIAAMP® Mini column (with VacConnectors). Switch on the vacuum pump. When all lysates have been drawn through the columns completely, switch off the vacuum pump and release the pressure to 0 mbar.
5. Transfer the QIAAMP® Mini column from the vacuum manifold into the 2 ml collection tube, and centrifuge for 1 min at full speed (20,000×g).
6. Make a mix of DNase I (100) and Buffer RDD (700) in a 1.5 ml microcentrifuge tube. Mix by gently flicking the tube, and centrifuge briefly to collect residual liquid from the sides of the tube.
7. Transfer the QIAAMP® Mini column back to its original position on the vacuum manifold. Pipet the DNase I incubation mix (80 µl) directly onto the QIAAMP® Mini column membrane, and incubate at ambient temperature (20-30° C.) for 20 min.
8. Wash the columns by adding 600 µl Buffer ACW1 to the QIAAMP® Mini column. Leave the lid of the column open, and switch on the vacuum pump. After all of Buffer ACW1 has been drawn through the QIAAMP® Mini column, switch off the vacuum pump and release the pressure to 0 mbar.
9. Apply 750µl Buffer ACW2 to the QIAAMP® Mini column. Leave the lid of the column open, and switch on the vacuum pump. After all of Buffer ACW2 has been drawn through the QIAAMP® Mini column, switch off the vacuum pump and release the pressure to 0 mbar.
10. Apply 750 µl of ethanol (96-100%) to the QIAAMP® Mini column. Leave the lid of the column open, and switch on the vacuum pump. After all of ethanol has been drawn through the spin column, switch off the vacuum pump and release the pressure to 0 mbar.
11. Wash the column again with 7500 ethanol.
12. Close the lid of the QIAAMP® Mini column. Remove it from the vacuum manifold, and discard the VacConnector. Place the QIAAMP® Mini column in a clean 2 ml collection tube, and centrifuge at full speed (20,000×g; 14,000 rpm) for 3 min.
13. Place the QIAAMP® Mini Column into a new 2 ml collection tube. Open the lid, and incubate the assembly at 56° C. for 10 min to dry the membrane completely.

14. Place the QIAAMP® Mini column in a clean 1.5 ml collection tube (provided) and discard the 2 ml collection tube from step 16.
15. Carefully apply 55 Buffer AVE to center of the membrane (recommended 20-150 µl
16. Close the lid and incubate at room temperature for 3 minutes.
17. Centrifuge at full speed (20,000×g; 14,000 rpm) for 1 min to elute the RNA.
18. Reapply the eluate to center of the membrane. Close the lid and incubate at room temperature for 3 minutes.
19. Centrifuge at full speed (20,000×g; 14,000 rpm) for 1 min to elute the RNA.

Example 8

PCR-Based Detection of Exosomes RNA Protocol

The resulting RNA can be analysed by qRT-PCR, gel electrophoresis, sequencing, microarray profiling analysis etc. The choice between one-step and two-step qRT-PCR comes down to convenience, sensitivity and assays design.

1-Step qRT-PCR:

One-step qRT-PCR combines the first-strand cDNA synthesis reaction and the qPCR reaction in the same tube, simplifying reaction setup and reducing the possibility of contamination. Gene-specific primers are required. Several 1-step RT-PCR reagents and enzymes are available. The protocol example herein is using the commercial available rTth kit "EZ rTth RNA PCR reagent Kit" (INVITROGEN®).

For a 50 ul 1-Step PCR Reaction Setup:

| Component | | Final concentration in 50 ul 1-Step PCR reaction |
|---|---|---|
| 5x TAQMAN ® EZ buffer | | 1x |
| 25 mM Mn(Oac) | | 3 mM |
| 10 mM dATP | | 300 uM |
| 10 mM dCTP | | 300 uM |
| 10 mM dGTP | | 300 uM |
| 10 mM dUTP | | 300 uM |
| Primer/Probe | Assay and target dependent | ~400-800 nM |
| 2.5 U/ul rTth DNA polymerase | | 5 U |
| 1 U/ul AMPERASE ® uracil-N-glycosylase | | 0.5 U |
| RNase free water | | To a final vol = 50 ul |

1. Mix the reagents on ice and centrifuge briefly. Aliquot into a 96-well plate.
2. Centrifuge briefly
3. Place the plate in the Real-Time PCR system (RochoROCHE® LC480) and run under the following Thermal Cycling conditions (ramp rate 4.4° C./s, except for cycling, where the ramp rate is 2.2° C./s)

| | | |
|---|---|---|
| UNG Treatment | 50° C. | 2 min |
| Reverse Transcription | 60° C. | 30 min |
| Deactivation of UNG | 95° C. | 5 min |
| Amplification (60 cycles) | 94° C. | 20 sec |
| | 60° C. | 60 sec (acquisition) |
| Cooling | 40° C. | 10 sec |

2-Step qRT-PCR:

Two-step qRT-PCR starts with the reverse transcription of either total RNA or poly(A)+RNA into cDNA using a reverse transcriptase (RT) This first-strand cDNA synthesis reaction can be primed using random hexamers, oligo(dT) or gene-specific primers. Several commercial kits are available for cDNA synthesis and subsequent qPCR. The protocol example herein is using the VILO™ cDNA synthesis kit (INVITROGEN®) for cDNA synthesis and the EXPRESS Supermix Mastermix (INVITROGEN®) and TAQMAN® Gene Expression Assay (APPLIED BIOSYSTEMS®) for qPCR analysis.

cDNA Synthesis

| Component | Final concentration |
|---|---|
| 5x VILO Reaction mix | 1x |
| 10X SuperScript ® enzyme mix | 1x |
| RNA | 1:1 of final reaction volume (e.g. 15 ul RNA into 30 ul reaction volume) Water to a final reaction of e.g. 30 |

4. Mix the reagents on ice and centrifuge briefly. Aliquot into a 96-well plate.
5. Centrifuge briefly
6. Place in a standard commercially available end-point PCR cycler.
7. Thermal cycling conditions: 25° C. 10 min, 42° C. for 2 hrs, 85° C., 5 min.

qPCR Analysis

| Component | Final concentration in 25 ul reaction volume |
|---|---|
| 2x EXRPESS qPCR supermix universal (APPLIED BIOSYSTEMS ® ) | 1x |
| 20x TAQMAN ® Assay | 1x |
| cDNA input | 2.5 ul |
| Nuclease free water | Total volume of 25 ul |

1. Cap the tube and invert it several times to mix the reaction components.
2. Centrifuge briefly.
3. Aliquot 22.5 µl into each well of a 96-well PCR plate (ROCHE®; LIGHTCYCLER® 480 Multiwell plate 96; Cat. no. 04 729 692 001).
4. Centrifuge the cDNA samples and add 2.5 µl cDNA to the respective wells.
5. Cover the 96-well plate with a film cover (provided with the PCR plates) and press it down firmly on the plate.
6. Centrifuge the plate briefly (2200×g; 30 sec)
7. Vortex for 15 sec on Eppendorf Mix mate 96 to mix the reagents and centrifuge briefly
8. Place the plate in the Real-Time PCR system (ROCHE® LC480) and run under the following Thermal Cycling conditions:

| | | |
|---|---|---|
| UDG Inactivation | 50° C. | 2 min |
| Denaturation | 95° C. | 5 min |
| Amplification (60 cycles) | 95° C. | 10 sec |
| | 60° C. | 50 sec |
| | 72° C. | 1 sec (acquisition) |
| Cooling | 40° C. | 10 sec |

Example 9

DIRECT™ mRNA Oligo(dT) Kit Protocol

Poly (A)+RNA makes up 1 to 2% of total RNA and can be separated by affinity chromatography on oligo (dT)-cellulose. Poly (A) tails form stable RNA-DNA hybrids with short chains of oligo (dT) that attach to various support matrices. High salt must be added to the chromatography buffer to stabilize the nucleic acid duplexes as only a few dT-A base pairs are formed. A low-salt buffer is used after nonpolyadenylated RNAs have been washed from the matrix. This buffer helps to destabilize the double-stranded structures and elute the poly (A)+RNAs from the resin[5].

The DYNABEADS® mRNA DIRECT™ kit (INVITROGEN®) protocol uses oligo(dT)25 residues covalently couple to the surface of DYNABEADS®.

Materials
- Lysis/binding buffer: 100 mM Tris-HCl pH 7.5, 500 mM LiCl, 10 mM EDTA pH 8, 1% LIDS
- Washing buffer A: 10 mM Tris-HCl pH 7.5, 0.15M LiCl, 1 mM EDTA, 0.1% LiDS
- Washing buffer B: 10 mM Tris-HCl pH 7.5, 0.15M LiCl, 1 mM EDTA
- Elution buffer: 10 mM Tris-HCL pH 7.5

Protocol
1. Add 3 volumes of lysis/binding buffer to 1 ml of RNA-containing particles. Pipette up and down to lyse.
1. Remove the Lysis/Binding Buffer from the pre-washed DYNABEADS® Oligo(dT)25 by placing on the magnet for 30 seconds, or until the suspension is clear. Remove the microtube from the magnet and add the sample lysate. Ensure the beads are without solution for minimum time.
3. Pipette to resuspend the beads completely in the sample lysate. Incubate with continuous mixing (rotating or roller mixer) for 3-5 min. at room temperature to allow the polyA tail of the mRNA to hybridize to the oligo (dT)25 on the beads. Increase the incubation time if the solution is viscous.
4. Place the vial on the magnet for 2 min. and remove the supernatant. If the solution is noticeably viscous, increase the time to approx. 10 min.
5. Wash the beads/mRNA complex two times with the appropriate volume of Washing Buffer A (see from table below) at room temperature. Use the magnet to separate the beads from the solution between each washing step.
6. Wash the beads/mRNA complex once with the appropriate volume of Washing Buffer B at room temperature. Use the magnet to separate the beads from the solution.
7. If the isolated mRNA is to be used in enzymatic downstream applications (e.g. RT-PCR), one extra wash in Wishing Buffer B is recommended. This should be followed by a final wash in the enzymatic buffer to be used (e.g. RT-PCR buffer without the enzyme or primers).
8. NOTE: Perform cDNA synthesis as recommended by the manufacturer of the reverse transcriptase. When using a thermostable reverse transcriptase and the bead-bound oligo (dT) as primer for first strand cDNA synthesis, an initial incubation at 50° C. for 5 minutes is necessary before proceeding at the recommended temperature.
9. If elution of mRNA from the beads is desired, add an appropriate volume of 10 mM Tris-HCl (Elution Buffer) and incubate at 65-80° C. for 2 min. Immediately place the tube on the magnet, transfer the supernatant containing the mRNA to a new RNase free tube and place this tube on ice.

Example 10

Exosomes Contain Polyadenylated RNA Species

1. Whole blood collected in EDTA tubes is centrifuged at 1500×g for 10 mins at 4° C., plasma is transferred into new tubes and centrifuged for a second time at 1500×g. This plasma is then transferred to a fresh tube and centrifuged for a third time, this time at 16,000×g for 10 mins at 4° C. The resultant supernatant now constitutes an acellular solution containing intact microvesicles
1. 2 ml of acellular solution prepared using the 3 step centrifugation protocol above was used to extract total RNA using the QIAAMP® kit protocol as described in Example Protocol 4.
2. 2 ml of acellular solution prepared using the 3 step centrifugation protocol above was used to extract mRNA using the DYNABEADS® mRNA DIRECT Kit (DYNAL® Biotech ASA, Oslo, Norway), Example 6.
3. The levels of GAPDH RNA in the RNA eluted from steps (2) and (3) were measured by 2-step PCR (Example Protocol 5) using a commercially available GAPDH primer-probe set available through APPLIED BIOSYSTEMS®.
4. The levels of GAPDH RNA in the two extraction methods were the same. Hence, it was concluded that exosome-derived RNA contains polyadenylated RNA species.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Aline et al. *Infect Immun* 2004, 72:4127-4137
Beauvillain et al. *Microbes Infect* 2007, 9:1614-1622
Chirgwin et al. *Biochemistry,* 18(24):5294-9, 1979
Chomczynski et al., *Analytical Biochemistry* 162(1):156-9, 1987
Colino et al. *Infect Immun* 2007, 75:220-230
Delcayre and Le Pecq., *Curr Opin Mol Ther* 2006, 8:31-38
Delcayre et al. *Blood Cells Mol Dis* 2005, 35:158-168
Gjerse et al. RNA Purification and Analysis: Sample Preparation, Extraction, Chromotography. 1st Edition. Weinheim, Germany: Wiley-VCH 2009
Hao et al. *Cell Mol Immunol* 2006, 3:205-211
Hao et al. *Immunology* 2007, 120:90-102
Hoorn et al. *Nephrology* (Carlton) 2005, 10:283-290
Keller et al. (2006), *Immunol. Lett.* 107(2):102-8
Kojima K, Ozawa S. Method for isolating and purifying nucleic acids. United State patent US 2002/0192667 A1, December 2002
Kuate et al. *Virology* 2007, 362:26-37
Lopez R. *Int Microbiol* 2006, 9:179-190
Makwana and Riordan, *CNS Drugs* 2007, 21:355-366
Pisitkun et al. *Mol Cell Proteomics* 2006, 5:1760-1771
Pisitkun et al. *Proc Natl Acad Sci USA* 2004, 101:13368-13373
Sambrook J and Russell D. Molecular Cloning: A Laboratory Manual. Third Edition. Cold Spring Harbor Laboratory Press, New York. 2001
Wolfers et al. *Nat Med* 2001, 7:297-303
Zitvogel et al. *Nat Med* 1998, 4:594-600

The invention claimed is:

1. A method of enriching for membranous microvesicles from a mammalian biological sample, the method comprising
   (a) subjecting the biological sample to a single step membranous microvesicle enrichment, wherein the single step consists of mechanical cellular rupture selected from the group consisting of
   (i) centrifugation;
   (ii) sonication, with or without the inclusion of surfactants;
   (iii) bead milling with or without the addition of surfactants using small glass;
   ceramic, zirconium or steel beads;
   (iv) homogenization;
   (v) using a nitrogen burst method;
   (vi) using a small probe ultrasound;
   (vii) using hypotonic shock;
   (viii) using high-shear mechanical methods;
   (ix) using rotor-stator disruptors;
   (x) using valve-type processors;
   (xi) using fixed geometry processors;
   (xii) using constant pressure processors;
   (xiii) using osmosis based electroporation; and
   (xiv) electropermeabilization,
   and wherein the mechanical cellular rupture selectively ruptures residual cells but not membranous microvesicles, and
   (b) lysing the enriched membranous microvesicles resulting from the single step in (a) to release their nucleic acid and protein content.

2. The method of claim 1, wherein the membranous microvesicles are exosomes.

3. The method of claim 1, wherein the mechanical cell rupture is performed using centrifugation at 15,000-17,000 g or bead milling.

4. The method of claim 3, wherein the bead is about 0.1 mm-0.5 mm in diameter and the sample is milled at about 20-40 Hz.

5. The method of claim 4, wherein the bead is a 0.1 mm glass bead and the milling is performed at about 30 Hz for about 2-5 minutes.

6. The method of claim 1, wherein the nucleic acid is mRNA and the method further comprises:
   isolating polyadenylated RNA.

7. The method of claim 6, wherein
   the polyadenylated RNA is isolated using oligo(dT) affinity chromatography; and
   wherein the method further comprises amplifying the isolated polyadenylated RNA.

8. The method of claim 7, wherein the amplification is selected from the group consisting of 1-step PCR and 2-step PCR.

9. The method of claim 8, wherein the amplification is 1-step PCR.

10. The method of claim 9, wherein the bead is about 0.1 mm-0.5 mm in diameter and the sample is milled at about 20-40 Hz or about 30 Hz.

11. The method of claim 10, wherein the bead is a 0.1 mm glass bead and the milling is performed at about 30 Hz for about 2-5 minutes.

12. The method of claim 9, wherein the mRNA has been eluted in about 35 µl of RNase free water and is amplified using 1-step PCR in a reaction volume of about 50 µl.

13. The method of claim 7, wherein isolation of the polyadenylated RNA comprises binding to a silica column, washing with Buffer ACWI (50-100% Guanidium chloride, Ethanol), Buffer ACW2 (50-100% Guanidium chloride, Ethanol) and ethanol and eluting in Buffer AVE (RNase-free water with 0.04% sodium-azide (v/v) and wherein:
   (a) the ACW2 buffer wash step is performed twice;
   (b) the ethanol wash step is performed twice;
   (c) the RNA is eluted in a final volume of about 35 µl; and
   (d) the eluate of step (c) and Buffer AVE are reapplied to the column.

14. The method of claim 1, wherein the biological sample is blood, serum, plasma, urine, stool, ascites, cerebrospinal fluid or saliva.

15. The method of claim 1, further comprising contacting an enzyme with the biological sample prior to or during the mechanical cellular rupture step (a).

16. The method of claim 15, wherein the enzyme is a ribonuclease or a deoxyribonuclease.

17. A method of isolating RNA from membranous microvesicles, comprising:
- selectively rupturing cells in a plasma sample to release cellular nucleic acid content;
- degrading the cellular nucleic acid content with an enzyme;
- neutralizing the enzyme;
- enriching membranous microvesicles, wherein the membranous microvesicles comprise RNA; and
- lysing the membranous microvesicles to release RNA.

18. The method of claim 17, wherein selective rupturing comprises centrifugation or bead milling.

19. The method of claim 17, wherein the enzyme is ribonuclease.

20. The method of claim 17, wherein the RNA is polyadenylated RNA.

* * * * *